United States Patent
Chen et al.

(10) Patent No.: US 9,920,057 B2
(45) Date of Patent: Mar. 20, 2018

(54) SUBSTITUTED PYRAZINO[1',2':1, 6]PYRIDO[3,4-B]INDOLES AS PHOSPHODIESTERASE TYPE 5 INHIBITORS

(71) Applicant: Chongqing University of Arts and Sciences, Chongqing (CN)

(72) Inventors: Zhongzhu Chen, Chongqing (CN); Zhigang Xu, Chongqing (CN); Dianyong Tang, Chongqing (CN)

(73) Assignee: Chongqing University of Arts and Sciences, Chongqing (CN)

(*) Notice: Subject to any disclaimer, the term of this patent is extended or adjusted under 35 U.S.C. 154(b) by 98 days.

(21) Appl. No.: 14/954,375

(22) Filed: Nov. 30, 2015

(65) Prior Publication Data

US 2016/0376273 A1    Dec. 29, 2016

Related U.S. Application Data

(63) Continuation of application No. PCT/CN2015/082507, filed on Jun. 26, 2015.

(51) Int. Cl.
| | |
|---|---|
| A61K 31/4985 | (2006.01) |
| C07D 487/04 | (2006.01) |
| C07D 471/14 | (2006.01) |

(52) U.S. Cl.
CPC .................. C07D 471/14 (2013.01)

(58) Field of Classification Search
CPC .......................... A61K 31/4985; C07D 487/04
USPC ........................... 514/250; 544/343; 549/464
See application file for complete search history.

(56) References Cited

U.S. PATENT DOCUMENTS

| | | | |
|---|---|---|---|
| 6,221,335 B1* | 4/2001 | Foster .................. | C07B 59/002 424/1.81 |
| 6,440,710 B1* | 8/2002 | Keinan .................. | C12P 13/02 435/147 |
| 6,603,008 B1* | 8/2003 | Ando .................. | C07D 405/14 546/269.7 |
| 6,911,542 B2* | 6/2005 | Orme .................. | C07D 471/14 544/343 |
| 7,517,990 B2* | 4/2009 | Ito .................. | C07B 59/002 546/184 |
| 2007/0082929 A1* | 4/2007 | Gant .................. | C07D 401/12 514/338 |
| 2007/0197695 A1* | 8/2007 | Potyen .................. | C08K 5/55 524/110 |

FOREIGN PATENT DOCUMENTS

| | | |
|---|---|---|
| CN | 102020522 A | 4/2011 |
| CN | 103980275 A | 8/2014 |
| CN | 104672288 A | 6/2015 |
| WO | 9519978 A1 | 7/1995 |
| WO | 0210166 A1 | 2/2002 |
| WO | 2014131855 A1 | 9/2014 |

OTHER PUBLICATIONS

Jordan, V. C. Nature Reviews: Drug Discovery, 2, 2003, 205.*
Hackam, et al. JAMA, 296(14), 2006, 1731-1732.*
Dyck, et al. Journal of Neurochemistry, 46(2), 1986, 399-404.*
Kushner, et al. Canadian Journal of Physiology and Pharmacology, 77(2), 1999, 79-88.*
Tonn, et al. Biological Mass Spectrometry, 22(11), 1993, 633-642.*
Wolen. Journal of Clinical Pharmacology, 26, 1986, 419-424.*
Browne. Journal of Clinical Pharmacology, 38, 1998, 213-220.*
Pieniaszek, et al. Journal of Clinical Pharmacology, 39, 1999, 817-825.*
International Search Report for PCT/CN2015/082507 dated Jun. 26, 2015.
Kern, et al., "Isolation and Structural Characterization of a New Tadalafil Analog (2-Hydroxyethylnortadalafil) Found in a Dietary Supplement", Journal of Pharmaceutical and Biomedical Analysis, 2015, pp. 99-103, vol. 103.
Ulloa et al., "Detection of a Tadalafil Analogue as an Adulterant in a Dietary Supplement for Erectile Dysfunction", Journal of Sexual Medicine, 2015, pp. 152-157, vol. 12.
Office Action for TW Application 104143514 dated Feb. 7, 2017.

* cited by examiner

*Primary Examiner* — Douglas M Willis
(74) *Attorney, Agent, or Firm* — Thompson Coburn LLP; J. Wendy Davis

(57) ABSTRACT

Disclosed is a compound represented by formula (I) or a pharmaceutically acceptable salt thereof as an inhibitor of phosphodiesterase type 5 and its therapeutic use in treating and/or preventing a disease or condition related with phosphodiesterase type 5 in a mammal wherein an inhibition of phosphodiesterase type 5 is considered beneficial

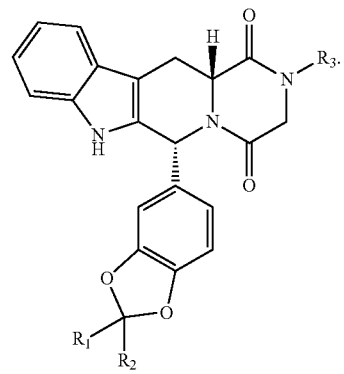

(I)

14 Claims, No Drawings

SUBSTITUTED PYRAZINO[1',2':1,6]PYRIDO[3,4-B]INDOLES AS PHOSPHODIESTERASE TYPE 5 INHIBITORS

CROSS REFERENCE TO RELATED APPLICATION

This application claims the benefit of PCT Patent Application No. PCT/CN2015/082507 filed on Jun. 26, 2015; which is incorporated herein by reference in its entirety.

TECHNICAL FIELD

The present application relates to a pharmaceutical field. In Particular, the present application relates to selective inhibitors of phosphodiesterase type 5 (PDE5) and their utilities in a variety of therapeutic areas wherein such inhibition is considered beneficial.

BACKGROUND

Erectile dysfunction (ED) has a significant impact on male mentality and physiology. It has been found that an inhibitor of PDE5 can effectively treat ED, such as Cialis from Eli Lilly and Company, whose chemical structure is shown as follows:

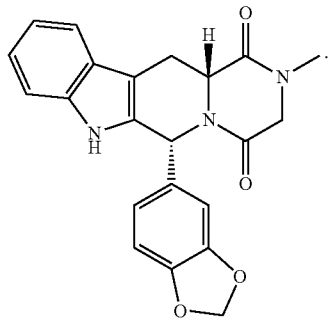 [SMILES: CN1CC(=O)N2[C@H](c3ccc4c(c3)OCO4)c3[nH]c4ccccc4c3C[C@@H]2C1=O]

PDE5 inhibitors were found to improve erectile dysfunction caused by a variety of factors, and as for the onset time, there is no significant difference among various PDE5 inhibitors. However, in respect of the half-life, there is a greater difference among these pharmaceutical compounds. For example, Cialis has a half-life of up to 24-36 hours in body, while Viagra from Pfizer and Levitra from Bayer both have half-life of about 4-5 hours.

Because of different half-life of a pharmaceutical compound, patients having different ages and different physical conditions will select pharmaceutical products with different half-lives to meet different requirements. However, there is a greater difference among the above-mentioned PDE5 inhibitors in half-life. Therefore, there is an urgent need for a novel PDE5 inhibitor.

SUMMARY

In one aspect, the present application is directed to a compound represented by formula (I) or a pharmaceutically acceptable salt thereof,

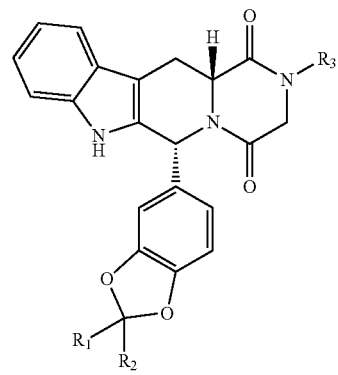

(I)

wherein
$R_1$ and $R_2$ are independently selected from the group consisting of hydrogen and deuterium;
$R_3$ is selected from the group consisting of hydrogen, -Q-OR$_6$, mercapto group and -Q-NR$_4$R$_5$;
Q is absent or $C_1$-$C_6$ alkylene;
$R_4$ and $R_5$ are independently selected from the group consisting of hydrogen, optionally substituted $C_1$-$C_6$ alkyl, —C(O)—$C_1$-$C_6$ alkyl, —C(O)—H, —S(O)$_2$—$C_1$-$C_6$ alkyl, —S(O)$_2$—H, —S(O)—$C_1$-$C_6$ alkyl, and —S(O)—H; and
$R_6$ is selected from the group consisting of hydrogen, optionally substituted $C_1$-$C_6$ alkyl, —C(O)—$C_1$-$C_6$ alkyl, —C(O)—H, —S(O)$_2$—$C_1$-$C_6$ alkyl, —S(O)$_2$—H, —S(O)—$C_1$-$C_6$ alkyl, and —S(O)—H;
with a provision that when both $R_1$ and $R_2$ are hydrogen, $R_3$ is -Q-NR$_4$R$_5$, Q is absent or $C_1$-$C_6$ alkylene, one of $R_4$ and $R_5$ is hydrogen and the other is selected from the group consisting of —S(O)$_2$—$C_1$-$C_6$ alkyl, —S(O)$_2$—H, —S(O)—$C_1$-$C_6$ alkyl, and —S(O)—H.

In another aspect, the present application is directed to a pharmaceutical composition, comprising a therapeutically effective amount of a compound represented by formula (I) or a pharmaceutically acceptable salt thereof, and a pharmaceutically acceptable carrier, excipient or diluent,

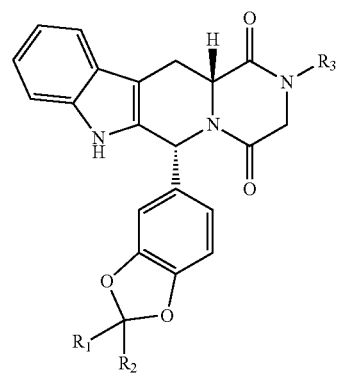

(I)

wherein
$R_1$ and $R_2$ are independently selected from the group consisting of hydrogen and deuterium;
$R_3$ is selected from the group consisting of hydrogen, -Q-OR$_6$, mercapto group and -Q-NR$_4$R$_5$;
Q is absent or $C_1$-$C_6$ alkylene;
$R_4$ and $R_5$ are independently selected from the group consisting of hydrogen, optionally substituted $C_1$-$C_6$ alkyl, —C(O)—C$_1$-C$_6$ alkyl, —C(O)—H, —S(O)$_2$—C$_1$-C$_6$ alkyl, —S(O)$_2$—H, —S(O)—C$_1$-C$_6$ alkyl, and —S(O)—H; and R$_6$ is selected from the group consisting of hydrogen, optionally substituted C$_1$-C$_6$ alkyl, —C(O)—C$_1$-C$_6$ alkyl, —C(O)—H, —S(O)$_2$—C$_1$-C$_6$ alkyl, —S(O)$_2$—H, —S(O)—C$_1$-C$_6$ alkyl, and —S(O)—H;

with a provision that when both R$_1$ and R$_2$ are hydrogen, R$_3$ is -Q-NR$_4$R$_5$, Q is absent or C$_1$-C$_6$ alkylene, one of R$_4$ and R$_5$ is hydrogen and the other is selected from the group consisting of —S(O)$_2$—C$_1$-C$_6$ alkyl, —S(O)$_2$—H, —S(O)—C$_1$-C$_6$ alkyl, and —S(O)—H.

In another aspect, the present application is directed to a use of a compound represented by formula (I) or a pharmaceutically acceptable salt thereof, or a pharmaceutical composition containing the same in the preparation of a medicament for treating and/or preventing a disease or condition related with phosphodiesterase type 5 in a mammal wherein an inhibition of phosphodiesterase type 5 is considered beneficial,

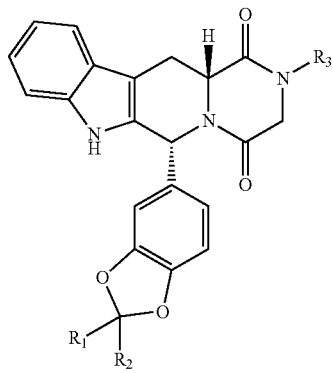

(I)

wherein

R$_1$ and R$_2$ are independently selected from the group consisting of hydrogen and deuterium;

R$_3$ is selected from the group consisting of hydrogen, -Q-OR$_6$, mercapto group and -Q-NR$_4$R$_5$;

Q is absent or C$_1$-C$_6$ alkylene;

R$_4$ and R$_5$ are independently selected from the group consisting of hydrogen, optionally substituted C$_1$-C$_6$ alkyl, —C(O)—C$_1$-C$_6$ alkyl, —C(O)—H, —S(O)$_2$—C$_1$-C$_6$ alkyl, —S(O)$_2$—H, —S(O)—C$_1$-C$_6$ alkyl, and —S(O)—H; and R$_6$ is selected from the group consisting of hydrogen, optionally substituted C$_1$-C$_6$ alkyl, —C(O)—C$_1$-C$_6$ alkyl, —C(O)—H, —S(O)$_2$—C$_1$-C$_6$ alkyl, —S(O)$_2$—H, —S(O)—C$_1$-C$_6$ alkyl, and —S(O)—H;

with a provision that when both R$_1$ and R$_2$ are hydrogen, R$_3$ is -Q-NR$_4$R$_5$, Q is absent or C$_1$-C$_6$ alkylene, one of R$_4$ and R$_5$ is hydrogen and the other is selected from the group consisting of —S(O)$_2$—C$_1$-C$_6$ alkyl, —S(O)$_2$—H, —S(O)—C$_1$-C$_6$ alkyl, and —S(O)—H.

In yet another aspect, the present application is directed to a method for treating and/or preventing a disease or condition related with phosphodiesterase type 5 in a mammal wherein an inhibition of phosphodiesterase type 5 is considered beneficial, comprising administering to the mammal in need thereof a therapeutically effective amount of a compound represented by formula (I) or a pharmaceutically acceptable salt thereof, or a pharmaceutical composition containing the same,

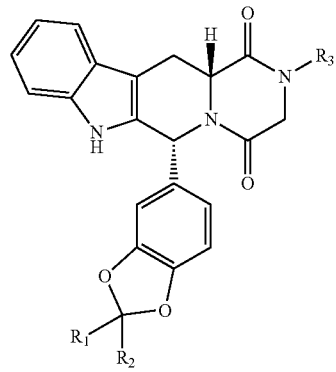

(I)

wherein

R$_1$ and R$_2$ are independently selected from the group consisting of hydrogen and deuterium, R$_3$ is selected from the group consisting of hydrogen, -Q-OR$_6$, mercapto group and -Q-NR$_4$R$_5$, Q is absent or C$_1$-C$_6$ alkylene, R$_4$ and R$_5$ are independently selected from the group consisting of hydrogen, optionally substituted C$_1$-C$_6$ alkyl, —C(O)—C$_1$-C$_6$ alkyl, —C(O)—H, —S(O)$_2$—C$_1$-C$_6$ alkyl, —S(O)$_2$—H, —S(O)—C$_1$-C$_6$ alkyl, and —S(O)—H, and R$_6$ is selected from the group consisting of hydrogen, optionally substituted C$_1$-C$_6$ alkyl, —C(O)—C$_1$-C$_6$ alkyl, —C(O)—H, —S(O)$_2$—C$_1$-C$_6$ alkyl, —S(O)$_2$—H, —S(O)—C$_1$-C$_6$ alkyl, and —S(O)—H;

with a provision that when both R$_1$ and R$_2$ are hydrogen, R$_3$ is -Q-NR$_4$R$_5$, Q is absent or C$_1$-C$_6$ alkylene, one of R$_4$ and R$_5$ is hydrogen and the other is selected from the group consisting of —S(O)$_2$—C$_1$-C$_6$ alkyl, —S(O)$_2$—H, —S(O)—C$_1$-C$_6$ alkyl, and —S(O)—H.

In yet another aspect, the present application is directed to a compound represented by formula (I) or a pharmaceutically acceptable salt thereof, or a pharmaceutical composition containing the same for use in a method for treating and/or preventing a disease or condition related with phosphodiesterase type 5 in a mammal wherein an inhibition of phosphodiesterase type 5 is considered beneficial,

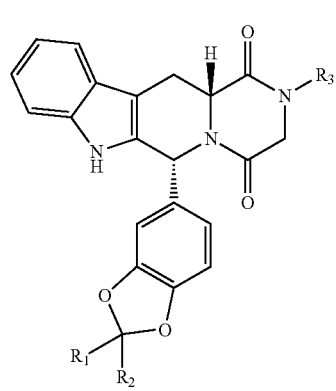

(I)

wherein

R$_1$ and R$_2$ are independently selected from the group consisting of hydrogen and deuterium;

$R_3$ is selected from the group consisting of hydrogen, -Q-OR$_6$, mercapto group and -Q-NR$_4$R$_5$;

Q is absent or $C_1$-$C_6$ alkylene;

$R_4$ and $R_5$ are independently selected from the group consisting of hydrogen, optionally substituted $C_1$-$C_6$ alkyl, —C(O)—$C_1$-$C_6$ alkyl, —C(O)—H, —S(O)$_2$—$C_1$-$C_6$ alkyl, —S(O)$_2$—H, —S(O)—$C_1$-$C_6$ alkyl, and —S(O)—H; and $R_6$ is selected from the group consisting of hydrogen, optionally substituted $C_1$-$C_6$ alkyl, —C(O)—$C_1$-$C_6$ alkyl, —C(O)—H, —S(O)$_2$—$C_1$-$C_6$ alkyl, —S(O)$_2$—H, —S(O)—$C_1$-$C_6$ alkyl, and —S(O)—H;

with a provision that when both $R_1$ and $R_2$ are hydrogen, $R_3$ is -Q-NR$_4$R$_5$, Q is absent or $C_1$-$C_6$ alkylene, one of $R_4$ and $R_5$ is hydrogen and the other is selected from the group consisting of —S(O)$_2$—$C_1$-$C_6$ alkyl, —S(O)$_2$—H, —S(O)—$C_1$-$C_6$ alkyl, and —S(O)—H.

In yet another aspect, the present application is directed to a method for treating and/or preventing erectile dysfunction in a human, comprising administering to the human in need thereof a therapeutically effective amount of a compound represented by formula (I) or a pharmaceutically acceptable salt thereof, or a pharmaceutical composition containing the same,

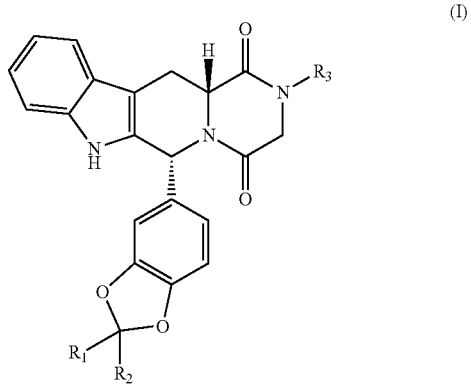

(I)

wherein $R_1$ and $R_2$ are independently selected from the group consisting of hydrogen and deuterium;

$R_3$ is selected from the group consisting of hydrogen, -Q-OR$_6$, mercapto group and -Q-NR$_4$R$_5$;

Q is absent or $C_1$-$C_6$ alkylene;

$R_4$ and $R_5$ are independently selected from the group consisting of hydrogen, optionally substituted $C_1$-$C_6$ alkyl, —C(O)—$C_1$-$C_6$ alkyl, —C(O)—H, —S(O)$_2$—$C_1$-$C_6$ alkyl, —S(O)$_2$—H, —S(O)—$C_1$-$C_6$ alkyl, and —S(O)—H; and $R_6$ is selected from the group consisting of hydrogen, optionally substituted $C_1$-$C_6$ alkyl, —C(O)—$C_1$-$C_6$ alkyl, —C(O)—H, —S(O)$_2$—$C_1$-$C_6$ alkyl, —S(O)$_2$—H, —S(O)—$C_1$-$C_6$ alkyl, and —S(O)—H;

with a provision that when both $R_1$ and $R_2$ are hydrogen, $R_3$ is -Q-NR$_4$R$_5$, Q is absent or $C_1$-$C_6$ alkylene, one of $R_4$ and $R_5$ is hydrogen and the other is selected from the group consisting of —S(O)$_2$—$C_1$-$C_6$ alkyl, —S(O)$_2$—H, —S(O)—$C_1$-$C_6$ alkyl, and —S(O)—H.

In another aspect, the present application is directed to a method for inhibiting the activity of phosphodiesterase type 5, comprising contacting a compound represented by formula (I) or a pharmaceutically acceptable salt thereof as defined in the above with phosphodiesterase type 5 in vitro or in vivo.

In another aspect, the present application is directed to a use of a compound represented by formula (I) or a pharmaceutically acceptable salt thereof as defined in the above as an inhibitor of phosphodiesterase type 5.

The compound represented by formula (I) or a pharmaceutically acceptable salt thereof according to the present application has a good inhibition effect on PDE5 and a suitable half-life and an appropriate biological metabolism in body. Therefore, it is prone to being developed as a clinical drug.

DETAILED DESCRIPTION

In the following description, certain specific details are included to provide a thorough understanding of various disclosed embodiments. One of ordinary skill in the relevant art, however, will recognize that the embodiments may be practiced without one or more of these specific details, or with other methods, components, materials etc.

Unless the context required otherwise, throughout the specification and claims which follows, the term "comprise" and variations thereof, such as "comprises" and "comprising" are to be construed in an open, inclusive sense, which is as "include, but not limited to".

Reference throughout this specification to "one embodiment", or "an embodiment", or "in another embodiment", or "in some embodiments" means that a particular referent feature, structure or characteristics described in connection with the embodiment is included in at least one embodiment. Therefore, the appearance of the phrases "in one embodiment" or "in the embodiment" or "in another embodiment" or "in some embodiments" in various places throughout this specification are not necessarily all referring to the same embodiment. Moreover, the particular features, structures or characteristics may be combined in any suitable manner in one or more embodiments.

It should be noted that, as used in this specification and the appended claims, the singular forms "a", "an" and "the" include plural referents unless the context clearly stated otherwise. It should be also noted that the use of "or" means "and/or" unless stated otherwise.

Definitions

As used in the specification and appended claims, unless specified to the contrary, the following terms have the meaning indicated:

"Mercapto group" refers to —SH.

"Cyano" refers to —CN.

"Amino" refers to —NH$_2$.

"Hydroxyl" refers to —OH.

"Halo" refers to bromo, chloro, fluoro or iodo.

"Carboxyl group" refers to —COOH.

"Sulfonic group" refers to —SO$_3$H.

"Sulfinic group" refers to —SO$_2$H.

"Alkyl" refers to a straight or branched hydrocarbon chain radical consisting solely of carbon and hydrogen atoms, containing no unsaturation, having from one to six carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), and the like. When specifically stated in the specification, an alkyl group may be optionally substituted by one or more of the following groups: alkyl, halo, cyano, hydroxyl, mercapto, amino, carboxyl, sulfonic group, and sulfuric group.

"Alkylene" or "alkylene chain" refers to a straight or branched divalent hydrocarbon chain linking the rest of the molecule to a radical group or linking two parts of the molecule, consisting solely of carbon and hydrogen, containing no unsaturation and having from one to six carbon atoms, e.g., —CH$_2$—, —CH$_2$—CH$_2$—, —CH$_2$—CH$_2$—CH$_2$—, n-butylene, and the like. The alkylene chain is attached to the rest of the molecule through a single bond and to the radical group through a single bond or is attached to two parts of the molecule through a single bond at each point of attachment.

"Optional" or "optionally" means that the subsequently described event of circumstances may or may not occur, and that the description includes instances where said event or circumstance occurs and instances in which it does not. For example, "optionally substituted alkyl" means that the alkyl radical may or may not be substituted and that the description includes both substituted alkyl radicals and alkyl radicals having no substitution ("unsubstituted").

The term "carrier" defines a compound that facilitates the incorporation of a compound into cells or tissues. For example, dimethylsulfoxide (DMSO) is generally used as a carrier, as it facilitates the uptake of many organic compounds into cells or tissues of an organism.

The term "pharmaceutically acceptable carrier" includes without limitation any adjuvant, carrier, excipient, glidant, sweetening agent, diluent, preservative, dye/colorant, flavor enhancer, surfactant, wetting agent, dispersing agent, suspending agent, stabilizer, isosmotic agent, solvent, or emulsifier, etc, which has been approved by the United States Food and Drug Administration as being acceptable for use in humans or animals and have no side effect on a pharmaceutical composition.

The term "pharmaceutically acceptable salts" means those salts which retain the biological effectiveness and properties of the PDE5 inhibitor used in the present application, and which are not biologically or otherwise undesirable. For example, a pharmaceutically acceptable salt does not interfere with the beneficial effect of an agent of the present application in inhibiting PDE5. The term "pharmaceutically acceptable salts" includes pharmaceutically acceptable acid addition salts and pharmaceutically acceptable base addition salts.

The term "a pharmaceutically acceptable acid addition salt" refers to those salts which retain the biological effectiveness and properties of the free bases, which are not biologically or otherwise undesirable, and which are formed with inorganic acids such as, but not limited to hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphanic acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleinic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like.

The term "mammal" includes humans and both domestic animals, such as laboratory animals and household pets (e.g. cats, dogs, swine, cattle, sheep, goats, horses, rabbits), and non-domestic animals such as wildlife and the like.

The term "pharmaceutical composition" refers to a formulation of a compound of the present application and a medium generally acceptable in the art for the delivery of the biologically active compound to mammals, e.g. humans. Such a medium includes all pharmaceutically acceptable carriers, diluents or excipients. The pharmaceutical composition is conducive to administration of a compound to an organism. There are various routes of administration of a compound or a pharmaceutical composition in the art including, but not limited to oral administration, injection administration, aerosol administration, parenteral administration and topical administration.

The term "pharmaceutically acceptable" defines a carrier, excipient or diluent that does not abrogate the biological activities and properties of a compound.

The term "therapeutically effective amount" refers to that amount of a compound of the present application which, when administered to a mammal, preferably a human, is sufficient to effect treatment of a disease or condition related with PDE5 in a mammal, preferably a human. The amount of a compound of the present application which constitutes a "therapeutically effective amount" will vary depending on the compound, the condition and its severity, and the age of the mammal to be treated, but can be determined routinely by one of ordinary skill in the art having regard to his own knowledge and to this disclosure.

The term "treating" or "treatment" as used herein covers the treatment of the disease or condition of interest in a mammal, preferably a human, having the disease or disorder of interest, and includes:

(i) preventing the disease or condition from occurring in a mammal, in particular, when such mammal is predisposed to the condition but has not yet been diagnosed as having it;

(ii) inhibiting the disease or condition, i.e. arresting its development; or (iii) relieving the disease or condition, i.e. causing regression of the disease or condition.

SPECIFIC EMBODIMENTS

In one aspect, the present application is directed to a compound represented by formula (I) or a pharmaceutically acceptable salt thereof,

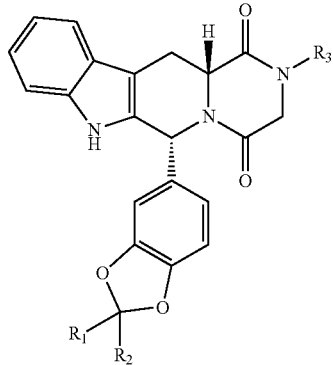

(I)

wherein $R_1$ and $R_2$ are independently selected from the group consisting of hydrogen and deuterium;

$R_3$ is selected from the group consisting of hydrogen, -Q-OR$_6$, mercapto group and -Q-NR$_4$R$_5$;

Q is absent or $C_1$-$C_6$ alkylene;

$R_4$ and $R_5$ are independently selected from the group consisting of hydrogen, optionally substituted $C_1$-$C_6$ alkyl, —C(O)—$C_1$-$C_6$ alkyl, —C(O)—H, —S(O)$_2$—$C_1$-$C_6$ alkyl, —S(O)$_2$—H, —S(O)—$C_1$-$C_6$ alkyl, and —S(O)—H; and $R_6$ is selected from the group consisting of hydrogen, optionally substituted $C_1$-$C_6$ alkyl, —C(O)—$C_1$-$C_6$ alkyl, —C(O)—H, —S(O)$_2$—$C_1$-$C_6$ alkyl, —S(O)$_2$—H, —S(O)—$C_1$-$C_6$ alkyl, and —S(O)—H;

with a provision that when both $R_1$ and $R_2$ are hydrogen, $R_3$ is -Q-NR$_4$R$_5$, Q is absent or $C_1$-$C_6$ alkylene, one of $R_4$ and $R_5$ is hydrogen and the other is selected from the group consisting of —S(O)$_2$—$C_1$-$C_6$ alkyl, —S(O)$_2$—H, —S(O)—$C_1$-$C_6$ alkyl, and —S(O)—H.

In some embodiments, the present application is directed to the compound represented by formula (I) or a pharmaceutically acceptable salt thereof, wherein $R_1$ and $R_2$ both are deuterium, or one of $R_1$ and $R_2$ is hydrogen and the other is deuterium;

$R_3$ is selected from the group consisting of hydrogen, -Q-OR$_6$, mercapto group and -Q-NR$_4$R$_5$;

Q is absent or $C_1$-$C_6$ alkylene;

$R_4$ and $R_5$ are independently selected from the group consisting of hydrogen; —C(O)—$C_1$-$C_6$ alkyl; —C(O)—H; —S(O)$_2$—$C_1$-$C_6$ alkyl; —S(O)$_2$—H; —S(O)—$C_1$-$C_6$ alkyl; —S(O)—H; and $C_1$-$C_6$ alkyl optionally substituted with a substituent selected from the group consisting of halo, cyano, hydroxyl, amino, mercapto, carboxyl, sulfonic group, and sulfinic group; and $R_6$ is selected from the group consisting of hydrogen; —C(O)—$C_1$-$C_6$ alkyl; —C(O)—H; —S(O)$_2$—$C_1$-$C_6$ alkyl; —S(O)$_2$—H; —S(O)—$C_1$-$C_6$ alkyl; —S(O)—H; and $C_1$-$C_6$ alkyl optionally substituted halo, cyano, hydroxyl, amino, mercapto, carboxyl, sulfonic group, and sulfinic group.

In some embodiments, the present application is directed to the compound represented by formula (I) or a pharmaceutically acceptable salt thereof, wherein $R_1$ and $R_2$ both are deuterium, or one of $R_1$ and $R_2$ is hydrogen and the other is deuterium;

$R_3$ is selected from the group consisting of hydrogen, -Q-OR$_6$, mercapto group and -Q-NR$_4$R$_5$;

Q is absent or $C_1$-$C_6$ alkylene that is represented by a formula "(CH$_2$)n", wherein n is an integer of 1-6;

$R_4$ and $R_5$ are independently selected from the group consisting of hydrogen, unsubstituted $C_1$-$C_6$ alkyl, —C(O)—$C_1$-$C_6$ alkyl, —C(O)—H, —S(O)$_2$—$C_1$-$C_6$ alkyl, —S(O)$_2$—H, —S(O)—$C_1$-$C_6$ alkyl, and —S(O)—H; and $R_6$ is selected from the group consisting of hydrogen, unsubstituted $C_1$-$C_6$ alkyl, —C(O)—$C_1$-$C_6$ alkyl, —C(O)—H, —S(O)$_2$—$C_1$-$C_6$ alkyl, —S(O)$_2$—H, —S(O)—$C_1$-$C_6$ alkyl, and —S(O)—H.

In some embodiments, the present application is directed to the compound represented by formula (I) or a pharmaceutically acceptable salt thereof, wherein $R_1$ and $R_2$ both are deuterium, or one of $R_1$ and $R_2$ is hydrogen and the other is deuterium;

$R_3$ is selected from the group consisting of hydrogen, -Q-OR$_6$, and -Q-NR$_4$R$_5$;

Q is absent or $C_1$-$C_6$ alkylene that is represented by a formula "(CH$_2$)n", wherein n is an integer of 1-6;

$R_4$ and $R_5$ are independently selected from the group consisting of hydrogen, unsubstituted $C_1$-$C_6$ alkyl, —C(O)—$C_1$-$C_6$ alkyl, —C(O)—H, —S(O)$_2$—$C_1$-$C_6$ alkyl, —S(O)$_2$—H, —S(O)—$C_1$-$C_6$ alkyl, and —S(O)—H; and $R_6$ is selected from the group consisting of hydrogen and unsubstituted $C_1$-$C_6$ alkyl.

In some embodiments, the present application is directed to the compound represented by formula (I) or a pharmaceutically acceptable salt thereof, wherein $R_1$ and $R_2$ both are deuterium, or one of $R_1$ and $R_2$ is hydrogen and the other is deuterium, and preferably $R_1$ and $R_2$ both are deuterium;

$R_3$ is -Q-NR$_4$R$_5$;

Q is absent or $C_1$-$C_6$ alkylene; and $R_4$ and $R_5$ are independently selected from the group consisting of hydrogen; —C(O)—$C_1$-$C_6$ alkyl; —C(O)—H; —S(O)$_2$—$C_1$-$C_6$ alkyl; —S(O)$_2$—H; —S(O)—$C_1$-$C_6$ alkyl; —S(O)—H; and $C_1$-$C_6$ alkyl optionally substituted with a substituent selected from the group consisting of halo, cyano, hydroxyl, amino, mercapto, carboxyl, sulfonic group, and sulfuric group.

In some embodiments, the present application is directed to the compound represented by formula (I) or a pharmaceutically acceptable salt thereof, wherein $R_1$ and $R_2$ both are deuterium, or one of $R_1$ and $R_2$ is hydrogen and the other is deuterium, and preferably $R_1$ and $R_2$ both are deuterium;

$R_3$ is -Q-NR$_4$R$_5$;

Q is absent or $C_1$-$C_6$ alkylene that is represented by a formula "(CH$_2$)n", wherein n is an integer of 1-6; and $R_4$ and $R_5$ are independently selected from the group consisting of hydrogen and unsubstituted $C_1$-$C_6$ alkyl.

In some embodiments, the present application is directed to the compound represented by formula (I) or a pharmaceutically acceptable salt thereof, wherein $R_1$ and $R_2$ both are hydrogen;

$R_3$ is -Q-NR$_4$R$_5$;

Q is absent or $C_1$-$C_6$ alkylene; and one of $R_4$ and $R_5$ is hydrogen and the other is selected from the group consisting of —S(O)$_2$—$C_1$-$C_6$ alkyl, —S(O)$_2$—H, —S(O)—$C_1$-$C_6$ alkyl, and —S(O)—H.

In some embodiments, the PDE5 inhibitor of the present application is preferably the following compounds:

Compound 1

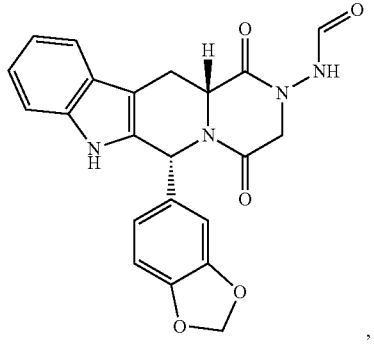

,

Compound 2

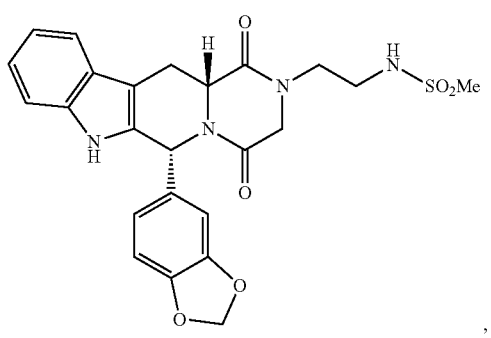

, and

Compound DDCI-01

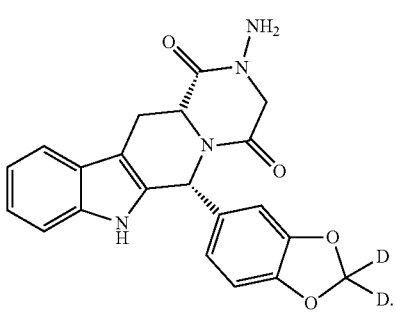

The compound represented by formula (I) according to the present application is a potent and selective inhibitor of PDE5, has a suitable half-life and an appropriate biological metabolism in body, and can meet a patient's requirement.

Pharmaceutical Compositions

In another aspect, the present application is directed to a pharmaceutical composition comprising a pharmaceutically acceptable carrier, excipient, or diluent and a therapeutically effective amount of a compound represented by formula (I) or a pharmaceutically acceptable salt thereof,

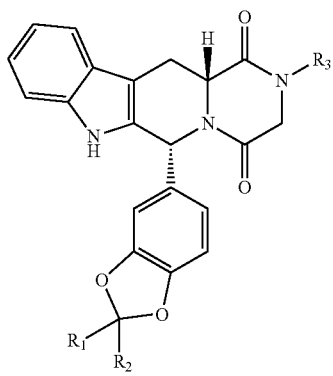

(I)

wherein $R_1$ and $R_2$ are independently selected from the group consisting of hydrogen and deuterium;

$R_3$ is selected from the group consisting of hydrogen, -Q-$OR_6$, mercapto group and -Q-$NR_4R_5$;

Q is absent or $C_1$-$C_6$ alkylene;

$R_4$ and $R_5$ are independently selected from the group consisting of hydrogen, optionally substituted $C_1$-$C_6$ alkyl, —C(O)—$C_1$-$C_6$ alkyl, —C(O)—H, —S(O)$_2$—$C_1$-$C_6$ alkyl, —S(O)$_2$—H, —S(O)—$C_1$-$C_6$ alkyl, and —S(O)—H; and $R_6$ is selected from the group consisting of hydrogen, optionally substituted $C_1$-$C_6$ alkyl, —C(O)—$C_1$-$C_6$ alkyl, —C(O)—H, —S(O)$_2$—$C_1$-$C_6$ alkyl, —S(O)$_2$—H, —S(O)—$C_1$-$C_6$ alkyl, and —S(O)—H;

with a provision that when both $R_1$ and $R_2$ are hydrogen, $R_3$ is -Q-$NR_4R_5$, Q is absent or $C_1$-$C_6$ alkylene, one of $R_4$ and $R_5$ is hydrogen and the other is selected from the group consisting of —S(O)$_2$—$C_1$-$C_6$ alkyl, —S(O)$_2$—H, —S(O)—$C_1$-$C_6$ alkyl, and —S(O)—H.

In some embodiments, the pharmaceutical composition of the present application comprises the compound represented by formula (I) or a pharmaceutically acceptable salt thereof, wherein $R_1$ and $R_2$ both are deuterium, or one of $R_1$ and $R_2$ is hydrogen and the other is deuterium, and preferably $R_1$ and $R_2$ both are deuterium;

$R_3$ is -Q-$NR_4R_5$;

Q is absent or $C_1$-$C_6$ alkylene; and $R_4$ and $R_5$ are independently selected from the group consisting of hydrogen; —C(O)—$C_1$-$C_6$ alkyl; —C(O)—H; —S(O)$_2$—$C_1$-$C_6$ alkyl; —S(O)$_2$—H; —S(O)—$C_1$-$C_6$ alkyl; —S(O)—H; and $C_1$-$C_6$ alkyl optionally substituted with a substituent selected from the group consisting of halo, cyano, hydroxyl, amino, mercapto, carboxyl, sulfonic group, and sulfuric group.

In some embodiments, the pharmaceutical composition of the present application comprises the compound represented by formula (I) or a pharmaceutically acceptable salt thereof, wherein $R_1$ and $R_2$ both are deuterium; $R_3$ is -Q-$NR_4R_5$; Q is absent; and $R_4$ and $R_5$ both are hydrogen.

In some embodiments, the pharmaceutical composition of the present application comprises the compound represented by formula (I) or a pharmaceutically acceptable salt thereof, wherein $R_1$ and $R_2$ both are hydrogen; $R_3$ is -Q-$NR_4R_5$; Q is absent or $C_1$-$C_6$ alkylene; and one of $R_4$ and $R_5$ is hydrogen and the other is selected from the group consisting of —S(O)$_2$—$C_1$-$C_6$ alkyl, —S(O)$_2$—H, —S(O)—$C_1$-$C_6$ alkyl, and —S(O)—H.

In some embodiments, the pharmaceutical composition is formulated into a dosage form suitable for oral administration, buccal administration, intravenous injection, intraperitoneal injection, subcutaneous injection, intramuscular injection, inhalation, or epidermal administration, preferable oral administration and buccal administration.

In some embodiments, the pharmaceutical composition is formulated into tablets, lozenges, pills, capsules, granules, powders, solutions, emulsions, suspensions, dispersions, syrups, gels, or aerosols.

In some embodiments, the pharmaceutical composition further comprises pharmaceutically acceptable surfactants, film forming substances, coating assistants, stabilizers, dyes, flavoring agents, fragrances, excipients, lubricants, disintegrants, glidants, solubilizers, fillers, solvents, diluents, suspending agents, osmoregulators, buffers, preservatives, antioxidants, sweetening agents, colorants and/or binders. Acceptable excipients, carriers or diluents for therapeutic use are well-known in the art, and are described, for example, in Remington's Pharmaceutical Sciences, 18th Ed., Mack Publishing Co., Easton, Pa. (1990), which is incorporated herein by reference in its entirety.

Pharmaceutical compositions of the present application may be manufactured in manner that is itself known, for example, by means of conventional mixing, dissolving, granulating, dragee-making, levigating, emulsifying, encapsulating, entrapping, or tabletting processes.

Pharmaceutical compositions for use in accordance with the present application therefore may be formulated by a conventional manner using one or more pharmaceutically acceptable carriers, excipients, diluents and/or auxiliaries which facilitate processing the active compounds into a pharmaceutical preparation. Proper formulation is dependent on the selected administration route. Any of the well-known techniques, carriers and excipients may be used as suitable and as understood in the art.

Methods of Treatment

In another aspect, the present application is directed to a use of a compound represented by formula (I) or a pharmaceutically acceptable salt thereof, or a pharmaceutical composition containing the same in the preparation of a medicament for treating and/or preventing a disease or condition related with phosphodiesterase type 5 in a mammal wherein an inhibition of phosphodiesterase type 5 is considered beneficial,

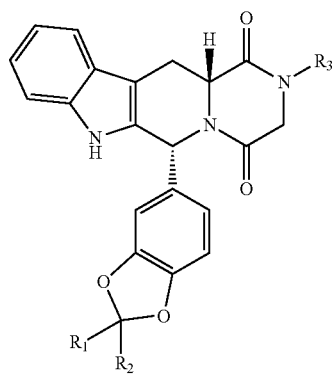

(I)

wherein $R_1$ and $R_2$ are independently selected from the group consisting of hydrogen and deuterium;

$R_3$ is selected from the group consisting of hydrogen, -Q-OR$_6$, mercapto group and -Q-NR$_4$R$_5$;

Q is absent or $C_1$-$C_6$ alkylene;

$R_4$ and $R_5$ are independently selected from the group consisting of hydrogen, optionally substituted $C_1$-$C_6$ alkyl, —C(O)—$C_1$-$C_6$ alkyl, —C(O)—H, —S(O)$_2$—$C_1$-$C_6$ alkyl, —S(O)$_2$—H, —S(O)—$C_1$-$C_6$ alkyl, and —S(O)—H; and $R_6$ is selected from the group consisting of hydrogen, optionally substituted $C_1$-$C_6$ alkyl, —C(O)—$C_1$-$C_6$ alkyl, —C(O)—H, —S(O)$_2$—$C_1$-$C_6$ alkyl, —S(O)$_2$—H, —S(O)—$C_1$-$C_6$ alkyl, and —S(O)—H;

with a provision that when both $R_1$ and $R_2$ are hydrogen, $R_3$ is -Q-NR$_4$R$_5$, Q is absent or $C_1$-$C_6$ alkylene, one of $R_4$ and $R_5$ is hydrogen and the other is selected from the group consisting of —S(O)$_2$—$C_1$-$C_6$ alkyl, —S(O)$_2$—H, —S(O)—$C_1$-$C_6$ alkyl, and —S(O)—H.

In some embodiments, the medicament of the present application comprises the compound represented by formula (I) or a pharmaceutically acceptable salt thereof, wherein $R_1$ and $R_2$ both are deuterium, or one of $R_1$ and $R_2$ is hydrogen and the other is deuterium, and preferably $R_1$ and $R_2$ both are deuterium;

$R_3$ is -Q-NR$_4$R$_5$;

Q is absent or $C_1$-$C_6$ alkylene; and $R_4$ and $R_5$ are independently selected from the group consisting of hydrogen; —C(O)—$C_1$-$C_6$ alkyl; —C(O)—H; —S(O)$_2$—$C_1$-$C_6$ alkyl; —S(O)$_2$—H; —S(O)—$C_1$-$C_6$ alkyl; —S(O)—H; and $C_1$-$C_6$ alkyl optionally substituted with a substituent selected from the group consisting of halo, cyano, hydroxyl, amino, mercapto, carboxyl, sulfonic group, and sulfuric group.

In some embodiments, the medicament of the present application comprises the compound represented by formula (I) or a pharmaceutically acceptable salt thereof, wherein $R_1$ and $R_2$ both are deuterium; $R_3$ is -Q-NR$_4$R$_5$; Q is absent; and $R_4$ and $R_5$ both are hydrogen.

In some embodiments, the medicament of the present application comprises the compound represented by formula (I) or a pharmaceutically acceptable salt thereof, wherein $R_1$ and $R_2$ both are hydrogen; $R_3$ is -Q-NR$_4$R$_5$; Q is absent or $C_1$-$C_6$ alkylene; and one of $R_4$ and $R_5$ is hydrogen and the other is selected from the group consisting of —S(O)$_2$—$C_1$-$C_6$ alkyl, —S(O)$_2$—H, —S(O)—$C_1$-$C_6$ alkyl, and —S(O)—H.

In some embodiments, the mammal is preferably a human.

In some embodiments, the disease or condition related with phosphodiesterase type 5 is erectile dysfunction.

In yet another aspect, the present application is directed to a method for treating and/or preventing a disease or condition related with phosphodiesterase type 5 in a mammal wherein an inhibition of phosphodiesterase type 5 is considered beneficial, comprising administering to the mammal in need thereof a therapeutically effective amount of a compound represented by formula (I) or a pharmaceutically acceptable salt thereof, or a pharmaceutical composition containing the same,

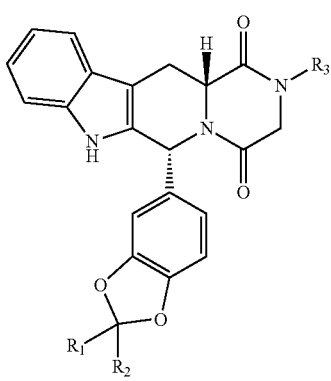

(I)

wherein

R₁ and R₂ are independently selected from the group consisting of hydrogen and deuterium;

R₃ is selected from the group consisting of hydrogen, -Q-OR₆, mercapto group and -Q-NR₄R₅;

Q is absent or $C_1$-$C_6$ alkylene;

R₄ and R₅ are independently selected from the group consisting of hydrogen, optionally substituted $C_1$-$C_6$ alkyl, —C(O)—$C_1$-$C_6$ alkyl, —C(O)—H, —S(O)₂—$C_1$-$C_6$ alkyl, —S(O)₂—H, —S(O)—$C_1$-$C_6$ alkyl, and —S(O)—H; and R₆ is selected from the group consisting of hydrogen, optionally substituted $C_1$-$C_6$ alkyl, —C(O)—$C_1$-$C_6$ alkyl, —C(O)—H, —S(O)₂—$C_1$-$C_6$ alkyl, —S(O)₂—H, —S(O)—$C_1$-$C_6$ alkyl, and —S(O)—H;

with a provision that when both R₁ and R₂ are hydrogen, R₃ is -Q-NR₄R₅, Q is absent or $C_1$-$C_6$ alkylene, one of R₄ and R₅ is hydrogen and the other is selected from the group consisting of —S(O)₂—$C_1$-$C_6$ alkyl, —S(O)₂—H, —S(O)—$C_1$-$C_6$ alkyl, and —S(O)—H.

In some embodiments, the compound represented by formula (I) or a pharmaceutically acceptable salt thereof used in the method for treating and/or preventing a disease or condition related with PDE5 is the compound represented by formula (I) or a pharmaceutically acceptable salt thereof, wherein R₁ and R₂ both are deuterium, or one of R₁ and R₂ is hydrogen and the other is deuterium, and preferably R₁ and R₂ both are deuterium; R₃ is -Q-NR₄R₅; Q is absent or $C_1$-$C_6$ alkylene; and R₄ and R₅ are independently selected from the group consisting of hydrogen; —C(O)—$C_1$-$C_6$ alkyl; —C(O)—H; —S(O)₂—$C_1$-$C_6$ alkyl; —S(O)₂—H; —S(O)—$C_1$-$C_6$ alkyl; —S(O)—H; and $C_1$-$C_6$ alkyl optionally substituted with a substituent selected from the group consisting of halo, cyano, hydroxyl, amino, mercapto, carboxyl, sulfonic group, and sulfuric group.

In some embodiments, the compound represented by formula (I) or a pharmaceutically acceptable salt thereof used in the method for treating and/or preventing a disease or condition related with PDE5 is the compound represented by formula (I) or a pharmaceutically acceptable salt thereof, wherein R₁ and R₂ both are deuterium; R₃ is -Q-NR₄R₅; Q is absent; and R₄ and R₅ both are hydrogen.

In some embodiments, the compound represented by formula (I) or a pharmaceutically acceptable salt thereof used in the method for treating and/or preventing a disease or condition related with PDE5 is the compound represented by formula (I) or a pharmaceutically acceptable salt, wherein R₁ and R₂ both are hydrogen; R₃ is -Q-NR₄R₅; Q is absent or $C_1$-$C_6$ alkylene; and one of R₄ and R₅ is hydrogen and the other is selected from the group consisting of —S(O)₂—$C_1$-$C_6$ alkyl, —S(O)₂—H, —S(O)—$C_1$-$C_6$ alkyl, and —S(O)—H.

In some embodiments, the mammal in the method for treating and/or preventing a disease or condition related with PDE5 is preferably a human.

In some embodiments, the disease or condition related with phosphodiesterase type 5 in the method for treating and/or preventing a disease or condition related with PDE5 is erectile dysfunction.

In yet another aspect, the present application is directed to a compound represented by formula (I) or a pharmaceutically acceptable salt thereof, or a pharmaceutical composition containing the same for use in a method for treating and/or preventing a disease or condition related with phosphodiesterase type 5 in a mammal wherein an inhibition of phosphodiesterase type 5 is considered beneficial,

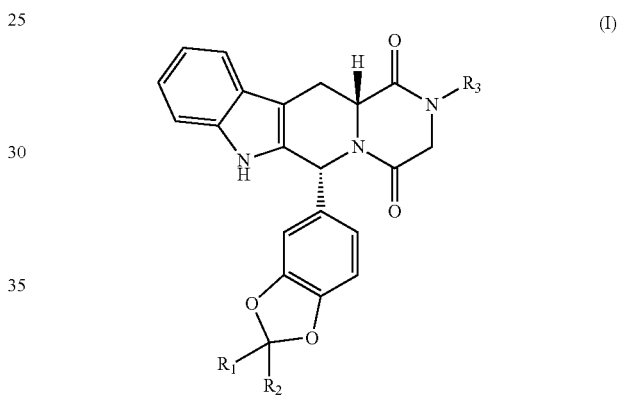

(I)

wherein

R₁ and R₂ are independently selected from the group consisting of hydrogen and deuterium;

R₃ is selected from the group consisting of hydrogen, -Q-OR₆, mercapto group and -Q-NR₄R₅;

Q is absent or $C_1$-$C_6$ alkylene;

R₄ and R₅ are independently selected from the group consisting of hydrogen, optionally substituted $C_1$-$C_6$ alkyl, —C(O)—$C_1$-$C_6$ alkyl, —C(O)—H, —S(O)₂—$C_1$-$C_6$ alkyl, —S(O)₂—H, —S(O)—$C_1$-$C_6$ alkyl, and —S(O)—H; and R₆ is selected from the group consisting of hydrogen, optionally substituted $C_1$-$C_6$ alkyl, —C(O)—$C_1$-$C_6$ alkyl, —C(O)—H, —S(O)₂—$C_1$-$C_6$ alkyl, —S(O)₂—H, —S(O)—$C_1$-$C_6$ alkyl, and —S(O)—H;

with a provision that when both R₁ and R₂ are hydrogen, R₃ is -Q-NR₄R₅, Q is absent or $C_1$-$C_6$ alkylene, one of R₄ and R₅ is hydrogen and the other is selected from the group consisting of —S(O)₂—$C_1$-$C_6$ alkyl, —S(O)₂—H, —S(O)—$C_1$-$C_6$ alkyl, and —S(O)—H.

In another aspect, the present application is directed to a method for inhibiting the activity of phosphodiesterase type 5, comprising contacting a compound represented by formula (I) or a pharmaceutically acceptable salt thereof with phosphodiesterase type 5 in vitro or in vivo,

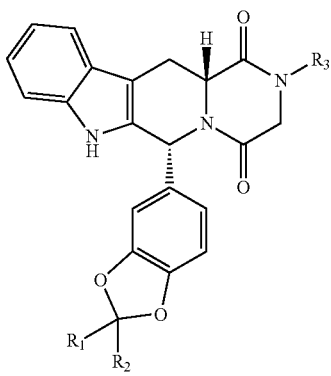

(I)

wherein $R_1$ and $R_2$ are independently selected from the group consisting of hydrogen and deuterium;

$R_3$ is selected from the group consisting of hydrogen, -Q-OR$_6$, mercapto group and -Q-NR$_4$R$_5$;

Q is absent or $C_1$-$C_6$ alkylene;

$R_4$ and $R_5$ are independently selected from the group consisting of hydrogen, optionally substituted $C_1$-$C_6$ alkyl, —C(O)—$C_1$-$C_6$ alkyl, —C(O)—H, —S(O)$_2$—$C_1$-$C_6$ alkyl, —S(O)$_2$—H, —S(O)—$C_1$-$C_6$ alkyl, and —S(O)—H; and $R_6$ is selected from the group consisting of hydrogen, optionally substituted $C_1$-$C_6$ alkyl, —C(O)—$C_1$-$C_6$ alkyl, —C(O)—H, —S(O)$_2$—$C_1$-$C_6$ alkyl, —S(O)$_2$—H, —S(O)—$C_1$-$C_6$ alkyl, and —S(O)—H;

with a provision that when both $R_1$ and $R_2$ are hydrogen, $R_3$ is -Q-NR$_4$R$_5$, Q is absent or $C_1$-$C_6$ alkylene, one of $R_4$ and $R_5$ is hydrogen and the other is selected from the group consisting of —S(O)$_2$—$C_1$-$C_6$ alkyl, —S(O)$_2$—H, —S(O)—$C_1$-$C_6$ alkyl, and —S(O)—H.

In yet another aspect, the present application is directed to a compound represented by formula (I) or a pharmaceutically acceptable salt thereof used as an inhibitor of phosphodiesterase type 5,

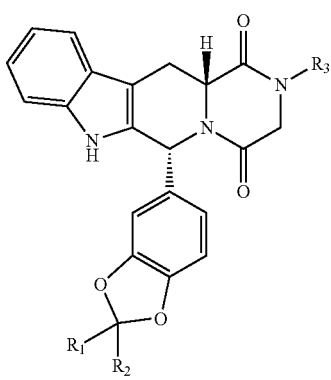

(I)

wherein $R_1$ and $R_2$ are independently selected from the group consisting of hydrogen and deuterium;

$R_3$ is selected from the group consisting of hydrogen, -Q-OR$_6$, mercapto group and -Q-NR$_4$R$_5$;

Q is absent or $C_1$-$C_6$ alkylene;

$R_4$ and $R_5$ are independently selected from the group consisting of hydrogen, optionally substituted $C_1$-$C_6$ alkyl, —C(O)—$C_1$-$C_6$ alkyl, —C(O)—H, —S(O)$_2$—$C_1$-$C_6$ alkyl, —S(O)$_2$—H, —S(O)—$C_1$-$C_6$ alkyl, and —S(O)—H; and $R_6$ is selected from the group consisting of hydrogen, optionally substituted $C_1$-$C_6$ alkyl, —C(O)—$C_1$-$C_6$ alkyl, —C(O)—H, —S(O)$_2$—$C_1$-$C_6$ alkyl, —S(O)$_2$—H, —S(O)—$C_1$-$C_6$ alkyl, and —S(O)—H;

with a provision that when both $R_1$ and $R_2$ are hydrogen, $R_3$ is -Q-NR$_4$R$_5$, Q is absent or $C_1$-$C_6$ alkylene, one of $R_4$ and $R_5$ is hydrogen and the other is selected from the group consisting of —S(O)$_2$—$C_1$-$C_6$ alkyl, —S(O)$_2$—H, —S(O)—$C_1$-$C_6$ alkyl, and —S(O)—H.

In yet another aspect, the present application is directed to a method for treating erectile dysfunction in a human, comprising administering to the human in need thereof a therapeutically effective amount of a compound represented by formula (I) or a pharmaceutically acceptable salt thereof, or a pharmaceutical composition containing the same,

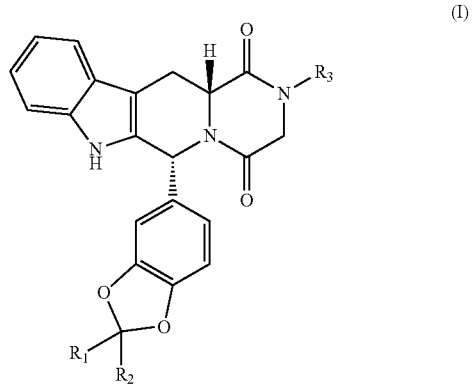

(I)

wherein $R_1$ and $R_2$ are independently selected from the group consisting of hydrogen and deuterium;

$R_3$ is selected from the group consisting of hydrogen, -Q-OR$_6$, mercapto group and -Q-NR$_4$R$_5$;

Q is absent or $C_1$-$C_6$ alkylene;

$R_4$ and $R_5$ are independently selected from the group consisting of hydrogen, optionally substituted $C_1$-$C_6$ alkyl, —C(O)—$C_1$-$C_6$ alkyl, —C(O)—H, —S(O)$_2$—$C_1$-$C_6$ alkyl, —S(O)$_2$—H, —S(O)—$C_1$-$C_6$ alkyl, and —S(O)—H; and $R_6$ is selected from the group consisting of hydrogen, optionally substituted $C_1$-$C_6$ alkyl, —C(O)—$C_1$-$C_6$ alkyl, —C(O)—H, —S(O)$_2$—$C_1$-$C_6$ alkyl, —S(O)$_2$—H, —S(O)—$C_1$-$C_6$ alkyl, and —S(O)—H;

with a provision that when both $R_1$ and $R_2$ are hydrogen, $R_3$ is -Q-NR$_4$R$_5$, Q is absent or $C_1$-$C_6$ alkylene, one of $R_4$ and $R_5$ is hydrogen and the other is selected from the group consisting of —S(O)$_2$—$C_1$-$C_6$ alkyl, —S(O)$_2$—H, —S(O)—$C_1$-$C_6$ alkyl, and —S(O)—H.

In some embodiments, the compound represented by formula (I) or a pharmaceutically acceptable salt thereof used in the method for treating erectile dysfunction is the compound represented by formula (I) or a pharmaceutically acceptable salt, wherein $R_1$ and $R_2$ both are deuterium, or one of $R_1$ and $R_2$ is hydrogen and the other is deuterium, and preferably $R_1$ and $R_2$ both are deuterium; $R_3$ is -Q-NR$_4$R$_5$; Q is absent or $C_1$-$C_6$ alkylene; and $R_4$ and $R_5$ are independently selected from the group consisting of hydrogen; —C(O)—$C_1$-$C_6$ alkyl; —C(O)—H; —S(O)$_2$—$C_1$-$C_6$ alkyl; —S(O)$_2$—H; —S(O)—$C_1$-$C_6$ alkyl; —S(O)—H; and $C_1$-$C_6$ alkyl optionally substituted with a substituent selected from the group consisting of halo, cyano, hydroxyl, amino, mercapto, carboxyl, sulfonic group, and sulfuric group.

In some embodiments, the compound represented by formula (I) or a pharmaceutically acceptable salt thereof used in the method for treating erectile dysfunction is the compound represented by formula (I) or a pharmaceutically acceptable salt, wherein $R_1$ and $R_2$ both are deuterium; $R_3$ is -Q-$NR_4R_5$; Q is absent; and $R_4$ and $R_5$ both are hydrogen.

In some embodiments, the compound represented by formula (I) or a pharmaceutically acceptable salt thereof used in the method for treating erectile dysfunction is the compound represented by formula (I) or a pharmaceutically acceptable salt, wherein $R_1$ and $R_2$ both are hydrogen; $R_3$ is -Q-$NR_4R_5$; Q is absent or $C_1$-$C_6$ alkylene; and one of $R_4$ and $R_5$ is hydrogen and the other is selected from the group consisting of —$S(O)_2$—$C_1$-$C_6$ alkyl, —$S(O)_2$—H, —$S(O)$—$C_1$-$C_6$ alkyl, and —$S(O)$—H.

Formulations, Routes of Administration, and Effective Doses

In yet another aspect, the present application relates to formulations comprising the compound represented by formula (I) or the pharmaceutically acceptable salt thereof, routes of administration and effective doses for the formulations. Such pharmaceutical formulations can be used to treat a disease or condition related with PDE5 as described above.

The compound represented by formula (I) or the pharmaceutically acceptable salt thereof of the present application can be administered as pharmaceutical formulations including but not limited to those suitable for oral (including buccal and sub-lingual), topical, or parenteral (including intramuscular, intradermal, intraperitoneal, subcutaneous and intravenous) administration or in a form suitable for administration by aerosolization, inhalation or insufflation. General information on drug delivery systems can be found in Ansel et al., Pharmaceutical Dosage Forms and Drug Delivery Systems (Lippencott Williams & Wilkins, Baltimore Md. (1999).

In various aspects, the pharmaceutical formulations includes carriers and excipients (including but not limited to buffers, carbohydrates, antioxidants, bacteriostats, chelating agents, suspending agents, thickening agents and/or preservatives), water, oils, saline solutions, flavoring agents, coloring agents, detackifiers and other acceptable additives, adjuvants, or binders, other pharmaceutically acceptable auxiliary substances as required to approximate physiological conditions, such as pH buffering agents, tonicity adjusting agents, emulsifying agents, wetting agents, preservatives and the like. It will be recognized that, while any suitable carrier known to those of ordinary skill in the art can be employed to administer the pharmaceutical formulations of the present application, the type of carrier will vary depending on the routes of administration.

The concentration of the compound can be adjusted, the pH of the solution buffered and the isotonicity adjusted to be compatible with intravenous injection, as is well known in the art.

The compound represented by formula (I) or the pharmaceutically acceptable salt thereof of the present application can be formulated as a sterile solution or suspension, in suitable vehicles, well known in the art. The pharmaceutical compositions can be sterilized by conventional, well-known sterilization techniques, or can be sterile filtered. The resulting aqueous solutions can be packaged for use as is, or lyophilized, the lyophilized preparation being combined with a sterile solution prior to administration.

For oral administration, the compound represented by formula (I) or the pharmaceutically acceptable salt thereof of the present application can be formulated readily by combining the active agent with pharmaceutically acceptable carriers well known in the art. Such carriers enable the agent of the present application to be formulated as tablets, pills, dragees, capsules, lozenges, liquids, gels, syrups, powders, suspensions, elixirs, and the like, for oral ingestion by a patient to be treated.

Pharmaceutical compositions suitable for use in the present application include compositions wherein the active ingredients are present in an effective amount, i.e., in an amount effective to achieve therapeutic and/or prophylactic benefit in a subject. The actual amount effective for a particular application will depend on the condition or conditions being treated, the condition of the subject, the formulation, and the route of administration, as well as other factors known to those of skill in the art. Determination of an effective amount of a PDE5 inhibitor is well within the capabilities of those skilled in the art, in light of the disclosure herein, and will be determined using routine optimization techniques.

The effective amount for use in humans can be determined from animal models. For example, a dose for humans can be formulated to achieve circulating, liver, topical and/or gastrointestinal concentrations that have been found to be effective in animals. One skilled in the art can determine the effective amount for human use, especially in light of the animal model experimental data described herein. Based on animal data, and other types of similar data, those skilled in the art can determine the effective amounts of compositions of the present application appropriate for humans.

The effective amount when referring to an inhibitor of PDE5 of the present application will generally mean the dose ranges, routes of administration, formulations, etc., that have been recommended or approved by any of the various regulatory or advisory organizations in the medical or pharmaceutical arts (e.g., FDA, SDA) or by the manufacturer or supplier.

Further, appropriate doses for a PDE5 inhibitor can be determined based on in vitro experimental results. For example, the in vitro potency of an agent in inhibiting PDE5 provides information useful in the development of effective in vivo dosages to achieve similar biological effects.

Having now generally described various aspects of the present application, the same will be more readily understood through reference to the following examples which are provided by way of illustration, and are not intended to be limiting, unless specified.

EXAMPLES

Example 1 Synthesis of Compound DDCI-01

Step 1. Synthesis of benzo[d][1,3]dioxole-2,2-$d_2$-5-carbaldehyde

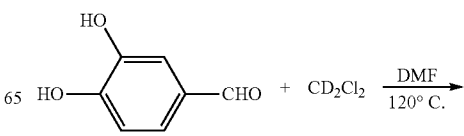

-continued

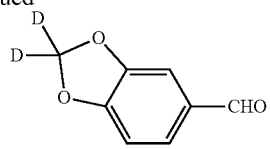

TABLE A

| Reagent | Mw. | eq. | Wt. or Vol. |
| --- | --- | --- | --- |
| 3,4-Dihydroxybenzaldehyde | 138 | 1.0 eq | 27.6 g (0.2 mol) |
| $CD_2Cl_2$ | 87 | 3.0 eq | 50.0 g (0.6 mol) |
| $Cs_2CO_3$ | 326 | 1.5 eq | 100 g |
| KI | 166 | 0.1 eq | 4.0 g |
| DMF | | | 200 mL |

To 500 mL round bottle flask equipped with a reflux condenser were added the reagents and solvents as showed in Table A. The resulting reaction mixture was heated and refluxed at 120° C. for 6 h under nitrogen atmosphere and stirring or until TLC indicated the completion of the reaction. Then, the reaction mixture was allowed to cool to room temperature, filtered to remove $Cs_2CO_3$ solid, and the filter cake was washed with dichloromethane. Subsequently, the filtrate was concentrated to dryness under reduced pressure, and the resulting residue was dissolved in dichloromethane, and washed sequentially with water and a saturated solution of NaCl. The organic phase was dried over anhydrous $MgSO_4$, filtered, and concentrated to dryness under reduced pressure to give a crude product. The crude product was purified by a silica gel column chromatography to afford 24.4 g of pure title compound as a white solid with 80% yield.

Step 2. Synthesis of methyl (1R,3R)-1-(benzo[d][1,3]dioxol-5-yl-2,2-d$_2$)-2,3,4,9-tetrahydro-1H-pyrido[3,4-b]indole-3-carboxylate hydrochloride

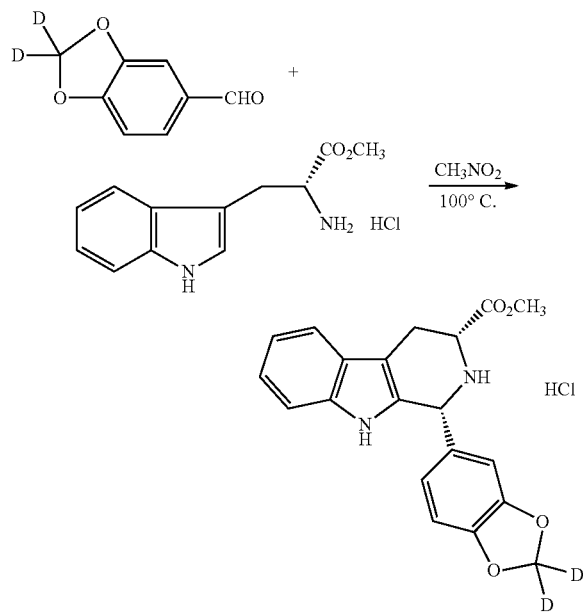

TABLE B

| reagent | Mw. | eq. | Wt. or Vol. |
| --- | --- | --- | --- |
| Product obtained from Step 1 | 152 | 1.0 eq | 24.4 g (0.16 mol) |
| D-tryptophan methyl ester hydrochloride | 255 | 1.0 eq | 41.0 g (0.16 mol) |
| $CH_3NO_2$ | | | 200 mL |

To 500 mL round bottle flask equipped with a reflux condenser were added the reagents and solvents as showed in Table B. The resulting reaction mixture was refluxed at 100° C. for 6 h under stirring or until TLC indicated the completion of the reaction. Then, the reaction mixture was cooled to room temperature, then cooled to 0° C. and was allowed to stand at 0° C. overnight to precipitate a solid. The resulting solid was filtered and washed with a small amount of $CH_3NO_2$ and subsequently with dichloromethane. After dried in vacuum, 60.0 g of title compound as a white solid was obtained with 96% of yield.

Step 3. Synthesis of methyl (1R,3R)-1-(benzo[d][1,3]dioxol-5-yl-2,2-d$_2$)-2-(2-chloroacetyl)-2,3,4,9-tetrahydro-1H-pyrido[3,4-b]indole-3-carboxylate

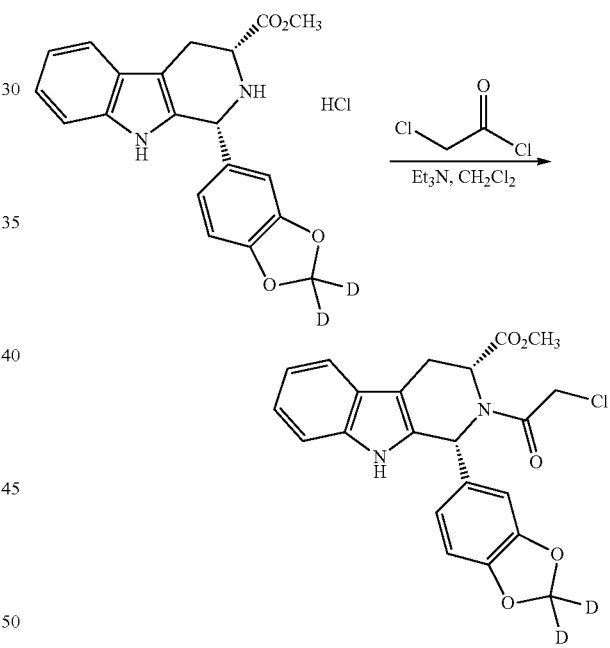

TABLE C

| Reagent | Mw. | eq. | Wt. or Vol. |
| --- | --- | --- | --- |
| Product obtained from Step 2 | 389 | 1.0 eq | 44.0 g (0.11 mol) |
| $Et_3N$ | 101 | 3.0 eq | 45 mL (0.33 mol) |
| chloroacetyl chloride | 113 | 1.5 | 17.0 g (0.22 mol) |
| $CH_2Cl_2$ | | | 500 mL |

400 mL dichloromethane, the product obtained from Step 2 (44.0 g, 0.11 mol) and $Et_3N$ (45.0 mL, 0.33 mol) were added to a 1000 mL of round bottle flask and stirred to obtain a clear solution at room temperature. After cooling to 0° C. in an ice bath, a solution of chloroacetyl chloride (17.0 g, 0.22 mol) in dichloromethane was slowly added dropwise, and meanwhile the reaction temperature is kept at 0° C. to 5° C. After the completion of addition, the resulting reaction mixture is continuously stirred in an ice bath (0° C. to 5° C.) until TLC indicated the completion of the reaction. The resulting reaction mixture was filtered and the filter cake was washed with a small amount of dichloromethane and dried to give 32.4 g of white solid that contains $Et_3N.HCl$ slat and is used for the next reaction without purification.

The filtrate was washed with 10% $K_2CO_3$ aqueous solution and then a saturated aqueous solution of NaCl. The resulting organic phase was dried over $MgSO_4$, filtered, and concentrated to dryness. The residue was recrystallized with $CH_3OH:H_2O=4:1$ to give 31.0 g of the title compound as a light brown solid.

Step 4. Synthesis of (6R,12aR)-2-amino-6-(benzo[d][1,3]dioxol-5-yl-2,2-$d_2$)-2,3,6,7,12,12a-hexahydropyrazino[1',2':1,6]pyrido[3,4-b]indole-1,4-dione

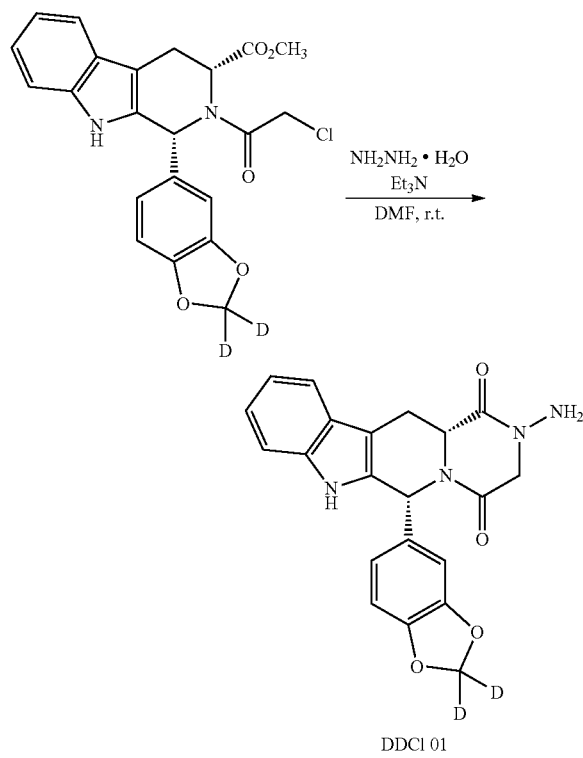

DDCl 01

TABLE D

| reagent | Mw. | eq. | Wt. or Vol. |
| --- | --- | --- | --- |
| Product obtained from Step 3 | 429 | 1.0 eq | 63.4 g |
| $Et_3N$ | 101 | 3.0 eq | 60 mL |
| hydrazine hydrate | 50 | 5.0 eq | 35 g |
| DMF | | | 400 mL |

To a 1000 mL round bottle flask were added the product obtained from Step 3 (63.4 g), $Et_3N$ (60 mL) and DMF, and then a solution of hydrazine hydrate (35.0 g) in DMF was slowly added dropwise at room temperature. The resulting reaction mixture was stirred overnight at room temperature until TLC indicated the completion of the reaction. 3 times volume of purified water was slowly added to the resulting reaction mixture at 0° C. with vigorous stirring for 2 h. A white solid was precipitated, filtered and washed with water and isopropyl alcohol to obtain a crude product. The crude product was dried in vacuum and diluted with a small amount of $CHCl_3$ and refluxed for 20 min. The solid was filtered again and dried in vacuum to give 35.5 g of pure title compound as a white solid with 82% yield for two steps.

$^1$HNMR (d-DMSO, 400M): 11.01 (s, 1H), 7.55 (d, J=7.6 Hz, 1H), 7.29 (d, J=8.0 Hz, 1H), 7.07 (t, J=7.2 Hz, 1H), 7.02 (t, J=7.2 Hz, 1H), 6.87 (d, J=1.2 Hz, 1H), 6.80 (dd, J=8.4, 1.6 Hz, 1H), 6.77 (d, J=8.0 Hz, 1H), 6.09 (s, 1H), 5.12 (s, 2H), 4.44 (dd, J=11.6, 3.6 Hz, 1H), 4.26 (dd, J=16.8, 1.6 Hz, 1H), 3.96 (d, J=17.2 Hz, 1H), 3.56 (dd, J=16.0, 4.4 Hz, 1H), 2.98 (dd, J=15.6, 12.0 Hz, 1H).

$^{13}$CNMR (d-DMSO, 100M): 166.76, 165.09, 147.53, 146.54, 137.56, 136.7, 134.50, 126.23, 121.73, 119.77, 119.35, 118.59, 111.79, 108.43, 107.40, 105.27, 56.05, 55.89, 53.81, 23.94.

Example 2 Synthesis of Compound 1

Except for omitting Step 1 and replacing the product obtained from Step 1 with piperonal (3,4-(methylenedioxy)benzaldehyde), Compound 1 is prepared by using a similar synthesis process to that in Example 1.

$^1$HNMR (500M, d-DMSO): δ 11.06 (s, 1H), 9.50 (s, 1H), 8.65 (s, 1H), 7.50 (d, J=7.7 Hz, 1H), 7.24 (d, J=7.9 Hz, 1H), 7.01 (t, J=7.3 Hz, 1H), 6.95 (t, J=7.3 Hz, 1H), 6.84 (s, 1H), 6.80-6.70 (m, 2H), 6.10 (s, 1H), 5.84 (s, 2H), 4.33 (dd, J=11.5, 3.8 Hz, 1H), 4.10 (d, J=17.1 Hz, 1H), 3.87 (d, J=17.2 Hz, 1H), 3.46-3.40 (m, 1H), 3.00-2.90 (m, 1H).

Example 3 Synthesis of Compound 2

Except for omitting Step 1 and replacing the product obtained from Step 1 with piperonal (3,4-(methylenedioxy)benzaldehyde), Compound 2 is prepared by using a similar synthesis process to that in Example 1.

$^1$HNMR (500M, d-DMSO): δ 11.16 (s, 1H), 7.52 (d, J=7.7 Hz, 1H), 7.31 (d, J=7.9 Hz, 1H), 7.07 (t, J=7.3 Hz, 1H), 7.01 (t, J=7.3 Hz, 1H), 6.90 (s, 1H), 6.80-6.70 (m, 2H), 6.11 (s, 1H), 5.91 (s, 2H), 4.41 (dd, J=11.5, 3.8 Hz, 1H), 4.10 (d, J=17.1 Hz, 1H), 3.91 (d, J=17.2 Hz, 1H), 3.51-3.40 (m, 1H), 3.21 (s, 3H), 3.02-2.95 (m, 1H), 3.00-2.95 (m, 4H).

Example 4 Inhibition Against PDE5

Method: $IC_{50}$ of an inhibition effect on PDE5A (E904, SIGMA-ALDRICH) of test compounds was tested by using Sildenafil (S1431, selleck) as a positive control sample and the method of Homogenous Time Resolve Fluoresce, HTF (Cat. No. 62GM2PEB, Cisbio.)

| Test compounds | IC$_{50}$ values |
|---|---|
| Cialis | 111.6 nM |
| DDCI-01 | 33.6 nM |
| DDCI02[note] | 566.2 nM |

[note]: the chemical structure of Compound DDCI02 is shown as follows:

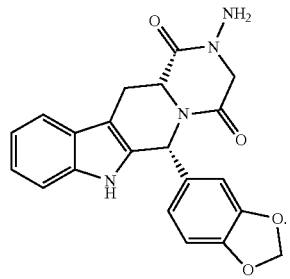

Example 5 Study on Pharmacokinetics

Experimental Methods

Stock Solution Preparation: Cialis 1.13 mg, DDCI02 1.15 mg, DDCI-01 1.23 mg were weighed and dissolved in 1.13 mL, 1.15 mL, 1.23 mL of DMSO respectively, to achieve the concentration of 1.00 mg·mL-1.

Sample Preparation Method: One step protein precipitation

Precipitant: ACN, with concentration of Verapamil (5.00 ng·mL-1)

Calibration Curve and QC samples Preparation: 5.00 μL each of the calibration or QC working solution and 45.0 μL of blank plasma were transferred into a 1.5-mL microcentrifuge tube. Final standard curve concentration levels were 1.00, 2.50, 5.00, 10.0, 50.0, 100, 500 and 1000 ng·mL-1. The QC concentration levels were 2.50 or 5.00, 50.0 and 800 ng·mL-1. Dilution QC was 5000 ng·mL-1.

Plasma Samples Preparation: Aliquots of 10.0 μL of real samples, calibration curve samples and QC samples were supplemented with 100 μL of precipitant. After vortexed for 3.00 min and centrifuged at 12000 rpm for 5.00 min, the supernatant 10 μL was injected for LC-MS/MS analysis.

Number of Rats/Group: 3/group

Administration Route: oral administration

Blood Collection Time: 0 min, 15 min, 30 min, 1 h, 2 h, 4 h, 6 h, 8 h, 24 h

| DDCI-01: | | | | | | | |
|---|---|---|---|---|---|---|---|
| PK Parameters | | PO-1 | PO-2 | PO-3 | Mean | SD | RSD (%) |
| Dose | mg·kg$^{-1}$ | | | 10.0 | | | |
| K$_{el}$ | h$^{-1}$ | 0.327 | 0.269 | 0.319 | 0.305 | 0.032 | 10 |
| t$_{1/2}$ | h | 2.12 | 2.58 | 2.17 | 2.29 | 0.251 | 11 |
| t$_{max}$ | h | 2.00 | 2.00 | 2.00 | 2.00 | 0 | 0 |
| C$_{max}$ | ng·mL$^{-1}$ | 1304 | 1574 | 1528 | 1468.7 | 144 | 10 |
| AUC$_{0-t}$ | h·ng·mL$^{-1}$ | 9970 | 11202 | 11080 | 10750 | 679 | 6.3 |
| AUC$_{0-inf}$ | h·ng·mL$^{-1}$ | 9976 | 11221 | 11087 | 10761 | 683 | 6.3 |
| AUMC$_{0-t}$ | h·h·ng·mL$^{-1}$ | 48497 | 50539 | 50911 | 49982 | 1300 | 2.6 |
| AUMC$_{0-inf}$ | h·h·ng·mL$^{-1}$ | 48665 | 51065 | 51110 | 50280 | 1399 | 2.8 |
| MRT$_{PO}$ | h | 4.88 | 4.55 | 4.61 | 4.68 | 0.174 | 3.7 |

| DDCI02 | | | | | | | |
|---|---|---|---|---|---|---|---|
| PK Parameters | | PO-7 | PO-8 | PO-9 | Mean | SD | RSD (%) |
| Dose | mg·kg$^{-1}$ | | | 10.0 | | | |
| K$_{el}$ | h$^{-1}$ | 0.143 | 0.221 | 0.216 | 0.193 | 0.0437 | 23 |
| t$_{1/2}$ | h | 4.85 | 3.14 | 3.21 | 3.73 | 0.969 | 26 |
| t$_{max}$ | h | 0.250 | 0.250 | 0.250 | 0.250 | 0 | 0 |
| C$_{max}$ | ng·mL$^{-1}$ | 4583 | 4288 | 5171 | 4681 | 450 | 10 |
| AUC$_{0-t}$ | h·ng·mL$^{-1}$ | 18125 | 15563 | 14723 | 16137 | 1772 | 11 |
| AUC$_{0-inf}$ | h·ng·mL$^{-1}$ | 18576 | 15617 | 14794 | 16329 | 1989 | 12 |
| AUMC$_{0-t}$ | h·h·ng·mL$^{-1}$ | 85428 | 56156 | 50008 | 63864 | 18926 | 30 |
| AUMC$_{0-inf}$ | h·h·ng·mL$^{-1}$ | 99393 | 57718 | 52047 | 69719 | 25854 | 37 |
| MRT$_{PO}$ | h | 5.35 | 3.70 | 3.52 | 4.19 | 1.01 | 24 |

| Cialis | | | | | | | |
|---|---|---|---|---|---|---|---|
| PK Parameters | | PO-1 | PO-2 | PO-3 | Mean | SD | RSD (%) |
| Dose | mg·kg$^{-1}$ | | | 10.0 | | | |
| K$_{el}$ | h$^{-1}$ | 0.200 | 0.197 | 0.346 | 0.248 | 0.0851 | 34 |
| t$_{1/2}$ | h | 3.46 | 3.51 | 2.00 | 2.99 | 0.858 | 29 |

-continued

| | | Cialis | | | | | |
|---|---|---|---|---|---|---|---|
| PK Parameters | | PO-1 | PO-2 | PO-3 | Mean | SD | RSD (%) |
| $t_{max}$ | h | 4.00 | 4.00 | 4.00 | 4.00 | 0 | 0 |
| $C_{max}$ | ng · mL$^{-1}$ | 747 | 676 | 1356 | 926 | 374 | 40 |
| $AUC_{0-t}$ | h · ng · mL$^{-1}$ | 8717 | 5993 | 11723 | 8811 | 2866 | 33 |
| $AUC_{0-inf}$ | h · ng · mL$^{-1}$ | 8812 | 6051 | 11729 | 8864 | 2839 | 32 |
| $AUMC_{0-t}$ | h · h · ng · mL$^{-1}$ | 53611 | 32747 | 71748 | 52702 | 19516 | 37 |
| $AUMC_{0-inf}$ | h · h · ng · mL$^{-1}$ | 56364 | 34440 | 71915 | 54240 | 18828 | 35 |
| $MRT_{PO}$ | h | 6.40 | 5.69 | 6.13 | 6.07 | 0.356 | 5.9 |

The above pharmacokinetics results indicated that both $C_{max}$ and Auc of DDCI-01 are more excellent than those of Cialis. Furthermore, the half-life ($T_{1/2}$) of DDCI-01 in SD rat is slightly shorter than that of Cialis and significantly shorter than that of DDCI02.

Example 6 Pharmacology Study on Erectile Function of Normal Rat

Measurement of Change in Blood Pressure and Intracavernous Pressure

Rats were anesthetized with 2% pentobarbital (3 mg/kg), then incision was made in the right side of neck, a PE-50 silicon tube connected with a pressure transducer was inserted into the carotid artery, to record the change of the blood pressure.

Via the incision in the inferior abdomen, exposing the lateral surface of prostate, a 23-gauge needle was inserted into the corpus cavernosum, filled with heparin (250 U/mL), and connected with a pressure sensor. The erectile activity was induced by a bipolar stainless-steel, stimulus parameters at a pulse width of 2.56 m, stimulation frequency of 7.98 Hz, current of 3 mA, stimulation duration of 40 s, and then record the intracavernous pressure (ICP).

Assessment of erectile function: ICP, BP, change of ICP and detumescence time were monitored though electric cavernous nerve stimulation at 2, 6 and 24 hours post dosing. Erectile function was evaluated by change of ICP and detumescence time.

TABLE 1

The blood pressure of study groups-2 hours after dosing (Mean ± SD)

| Group | BP before stimulation (mmHg)# | BP after stimulation (mmHg) | Change of BP (mmHg) |
|---|---|---|---|
| Vehicle | 102.44 ± 13.66 | 52.17 ± 14.97 | 50.27 ± 5.17 |
| Calais | 100.98 ± 4.48 | 64.14 ± 9.86 | 36.85 ± 7.34* |
| DDCI-01 Low dose | 97.43 ± 11.45 | 63.89 ± 2.93 | 33.54 ± 13.57* |
| DDCI-01 Middle dose | 96.49 ± 7.55 | 70.38 ± 7.82 | 26.12 ± 3.04** |
| DDCI-01 High dose | 91.86 ± 21.57 | 60.97 ± 19.95 | 30.89 ± 4.09* |

Note:
*P < 0.05, **P < 0.01 compared with Vehicle group.

TABLE 2

The intracavernous pressure of study groups-2 hours after dosing (Mean ± SD)

| Group | ICP before stimulation (mmHg) | ICP after stimulation (mmHg) | Change of ICP (mmHg) |
|---|---|---|---|
| Vehicle | 8.81 ± 3.06 | 26.55 ± 4.33 | 18.75 ± 4.48 |
| Calais | 7.38 ± 1.75 | 39.19 ± 8.58* | 31.82 ± 7.63* |
| DDCI-01 Low dose | 11.48 ± 4.57 | 42.86 ± 5.14* | 31.38 ± 3.09* |
| DDCI-01 Middle dose | 8.49 ± 2.06 | 41.58 ± 7.94* | 33.09 ± 7.46* |
| DDCI-01 High dose | 11.05 ± 3.25 | 52.25 ± 9.49** | 41.20 ± 9.83** |

Note:
*P < 0.05, **P < 0.01 compared with Vehicle group.

TABLE 3

The detumescence time of study groups-2 hours after dosing (Mean ± SD)

| Group | Change of BP/change of ICP | Detumescence Time(s) |
|---|---|---|
| Vehicle | 38.14 ± 13.17 | 9.75 ± 4.92 |
| Calais | 89.75 ± 33.30 | 40.50 ± 21.14* |
| DDCI-01 Low dose | 105.52 ± 41.17* | 38.00 ± 10.42* |
| DDCI-01 Middle dose | 128.64 ± 35.20* | 40.75 ± 4.79* |
| DDCI-01 High dose | 136.85 ± 41.98** | 101.00 ± 21.56** |

Note:
*P < 0.05, **P < 0.01 compared with Vehicle group.

TABLE 4

The blood pressure of study groups-6 hours after dosing (Mean ± SD)

| Group | BP before stimulation (mmHg) | BP after stimulation (mmHg) | Change of BP (mmHg) |
|---|---|---|---|
| Vehicle | 95.97 ± 4.28 | 52.58 ± 1.62 | 43.40 ± 4.78 |
| Calais | 91.20 ± 28.48 | 58.14 ± 14.30 | 33.07 ± 17.13 |
| DDCI-01 Low dose | 95.73 ± 18.25 | 61.78 ± 17.93 | 33.95 ± 3.20 |
| DDCI-01 Middle dose | 92.91 ± 19.51 | 61.03 ± 12.64 | 31.88 ± 7.39 |
| DDCI-01 High dose | 76.38 ± 21.11 | 50.09 ± 22.36 | 26.29 ± 1.54 |

Note:
Compared with Vehicle group, all no significance.

TABLE 5

The intracavernous pressure of study groups-6 hours after dosing (Mean ± SD)

| Group | ICP before stimulation (mmHg) | ICP after stimulation (mmHg) | Change of ICP (mmHg) |
|---|---|---|---|
| Vehicle | 8.78 ± 2.46 | 25.37 ± 3.87 | 16.59 ± 5.11 |
| Calais | 7.61 ± 1.53 | 41.76 ± 6.49* | 34.15 ± 6.99* |
| DDCI-01 Low dose | 8.98 ± 3.06 | 40.36 ± 5.92* | 31.38 ± 7.73* |

TABLE 5-continued

The intracavernous pressure of study groups-6 hours after dosing (Mean ± SD)

| Group | ICP before stimulation (mmHg) | ICP after stimulation (mmHg) | Change of ICP (mmHg) |
|---|---|---|---|
| DDCI-01 Middle dose | 6.72 ± 3.14 | 40.21 ± 8.37* | 33.49 ± 8.09* |
| DDCI-01 High dose | 9.20 ± 8.79 | 50.94 ± 11.12** | 41.74 ± 7.92** |

Note:
*$P < 0.05$, **$P < 0.01$ compared with Vehicle group.

TABLE 6

The detumescence time of study groups-6 hours after dosing (Mean ± SD)

| Group | Change of BP/change of ICP | Detumescence Time(s) |
|---|---|---|
| Vehicle | 39.30 ± 15.86 | 9.50 ± 2.52 |
| Calais | 117.16 ± 42.07* | 44.25 ± 13.35** |
| DDCI-01 Low dose | 94.70 ± 33.16* | 47.75 ± 11.79* |
| DDCI-01 Middle dose | 106.19 ± 16.03* | 48.00 ± 23.85* |
| DDCI-01 High dose | 159.65 ± 33.86** | 64.00 ± 19.37** |

Note:
*$P < 0.05$, **$P < 0.01$ compared with Vehicle group.

TABLE 7

The blood pressure of study groups-24 hours after dosing (Mean ± SD)

| Group | BP before stimulation (mmHg) | BP after stimulation (mmHg) | Change of BP (mmHg) |
|---|---|---|---|
| Vehicle | 100.82 ± 10.18 | 61.53 ± 12.03 | 39.30 ± 3.70 |
| Calais | 112.26 ± 7.30 | 78.00 ± 2.68 | 34.26 ± 7.18 |
| DDCI-01 Low dose | 108.36 ± 8.89 | 72.34 ± 12.33 | 36.03 ± 10.90 |
| DDCI-01 Middle dose | 102.18 ± 15.12 | 69.85 ± 12.70 | 32.33 ± 8.76 |
| DDCI-01 High dose | 94.16 ± 9.79 | 52.95 ± 14.12 | 41.21 ± 11.98 |

Note:
Compared with Vehicle group, all no significance.

TABLE 8

The intracavernous pressure of study groups-24 hours after dosing (Mean ± SD)

| Group | ICP before stimulation (mmHg) | ICP after stimulation (mmHg) | Change of ICP (mmHg) |
|---|---|---|---|
| Vehicle | 7.42 ± 2.26 | 27.02 ± 5.41 | 19.61 ± 3.44 |
| Calais | 7.63 ± 4.03 | 43.01 ± 6.19** | 35.38 ± 4.55** |
| DDCI-01 Low dose | 12.91 ± 5.02 | 43.55 ± 5.05** | 30.65 ± 0.98** |
| DDCI-01 Middle dose | 8.41 ± 1.86 | 40.00 ± 5.56** | 31.58 ± 5.75** |
| DDCI-01 High dose | 9.41 ± 3.81 | 52.77 ± 2.07** | 43.36 ± 4.90** |

Note:
**$P < 0.01$ compared with Vehicle group.

TABLE 9

The detumescence time of study groups-24 hours after dosing (Mean ± SD)

| Group | Change of BP/change of ICP | Detumescence Time(s) |
|---|---|---|
| Vehicle | 49.67 ± 5.59 | 8.75 ± 1.71 |
| Calais | 107.99 ± 32.42 | 41.25 ± 10.34* |
| DDCI-01 Low dose | 92.05 ± 31.72 | 23.75 ± 12.84 |
| DDCI-01 Middle dose | 106.03 ± 44.12 | 41.25 ± 14.50* |
| DDCI-01 High dose | 113.00 ± 38.23 | 60.75 ± 24.14** |

Note:
*$P < 0.05$, **$P < 0.01$ comparing with Vehicle group.

Experimental results in Tables 1-9 shows that after the test compound DDCI-01 is administered to the normal rat model, all three different doses of DDCI-01, including high, middle, and low doses, significantly improved the erectile function of the normal rat model by prolonging the detumescence time and significantly increasing the ICP in the normal rat model.

Example 7 The Efficacy Study of DDCI-01

Experiment Procedure 1.1.1 Compound Preparation

Serial dilute compounds in DMSO 3-fold serial dilute Cialis and DDCI-01 from 10 mM of stock solution in DMSO;

1.1.2 Compound Treatment i. Supplement 99 µl assay buffer per well, then add 1 µl compound in DMSO dilution to wells of V96 MicroWell Plates and uniformly mix;

ii. Add 5 µl compound in assay buffer dilution to each well of 96-well microplate;

the final concentration of compound as below:

10000, 3333, 1111, 370.4, 123.5, 41.2, 13.7, 4.6, 1.5, 0.51, 0.17 [nM];

The inhibitory potential of test compounds on several types of phosphodiesterase (PDE) activity is determined according to the protocol of assay kit. The screening results are shown in Table 10.

TABLE 10 the inhibition effect of test compounds on several types of PDE activity

| | IC50 (µM) | |
|---|---|---|
| PDE | Cialis (ref.) | DDCI-01 |
| PDE1A | >10 | >10 |
| PDE2A | >10 | >10 |
| PDE3A | >10 | >10 |
| PDE3A | >10 | >10 |
| PDE4A | >10 | >10 |
| PDE6C | 12.53 | 14.67 |
| PDE7A | >10 | >10 |
| PDE11A | 1.60 | 2.64 |

The above results show that among the 7 other PDE isoforms, DDCI-01 showed weak inhibitory activity against PDE6C (IC50>10 µM) and PDE11A (IC50=2.6 µM), while had no inhibition effect (0% inhibition at 10 µM) on PDE1A, 2A, 3A, 4A1A, and 7A.

What is claimed is:

1. A compound represented by formula (I):

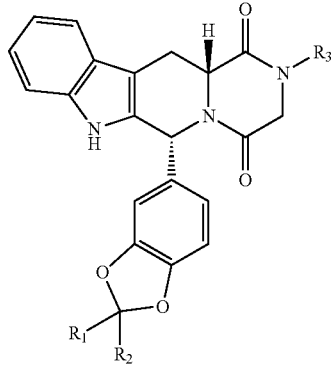

(I)

or a pharmaceutically acceptable salt thereof,
wherein:
$R_1$ and $R_2$ are both deuterium, or one of $R_1$ and $R_2$ is hydrogen and the other is deuterium;
$R_3$ is selected from the group consisting of hydrogen, -Q-OR$_6$, mercapto and -Q-NR$_4$R$_5$;
Q is absent or $C_1$-$C_0$ alkylene;
$R_4$ and $R_5$ are independently selected from the group consisting of hydrogen, —C(O)—$C_1$-$C_6$ alkyl, —C(O)—H, —S(O)$_2$—$C_1$-$C_6$ alkyl, —S(O)$_2$—H, —S(O)—$C_1$-$C_6$ alkyl, —S(O)—H, and $C_1$-$C_6$ alkyl, wherein said $C_1$-$C_6$ alkyl is unsubstituted or substituted with a substituent selected from the group consisting of halo, cyano, hydroxy, amino, mercapto, carboxy, sulfonic acid, and sulfinic acid; and
$R_6$ is selected from the group consisting of hydrogen, —C(O)—$C_1$-$C_6$ alkyl, —C(O)—H, —S(O)$_2$—$C_1$-$C_6$ alkyl, —S(O)$_2$—H, —S(O)—$C_1$-$C_6$ alkyl, —S(O)—H, and $C_1$-$C_6$ alkyl, wherein said $C_1$-$C_6$ alkyl is unsubstituted or substituted with a substituent selected from the group consisting of halo, cyano, hydroxy, amino, mercapto, carboxy, sulfonic acid, and sulfinic acid.

2. The compound of claim 1, wherein:
$R_3$ is selected from the group consisting of hydrogen, -Q-OR$_6$, mercapto and -Q-NR$_4$R$_5$;
$R_4$ and $R_5$ are independently selected from the group consisting of hydrogen, —C(O)—$C_1$-$C_6$ alkyl, —C(O)—H, —S(O)$_2$—$C_1$-$C_6$ alkyl, —S(O)$_2$—H, —S(O)—$C_1$-$C_6$ alkyl, —S(O)—H and $C_1$-$C_6$ alkyl, wherein said $C_1$-$C_6$ alkyl is substituted with a substituent selected from the group consisting of halo, cyano, hydroxy, amino, mercapto, carboxy, sulfonic acid and sulfinic acid; and
$R_6$ is selected from the group consisting of hydrogen, —C(O)—$C_1$-$C_6$ alkyl, —C(O)—H, —S(O)$_2$—$C_1$-$C_6$ alkyl, —S(O)$_2$—H, —S(O)—$C_1$-$C_6$ alkyl, —S(O)—H and $C_1$-$C_6$ alkyl, wherein said $C_1$-$C_6$ alkyl is substituted with a substituent selected from the group consisting of halo, cyano, hydroxy, amino, mercapto, carboxy, sulfonic acid and sulfinic acid.

3. The compound of claim 1, wherein:
$R_3$ is selected from the group consisting of hydrogen, -Q-OR$_6$, mercapto and -Q-NR$_4$R$_5$;
Q is absent or (CH$_2$)$_n$, wherein n is 1, 2, 3, 4, 5 or 6;
$R_4$ and $R_5$ are independently selected from the group consisting of hydrogen, —C(O)—$C_1$-$C_6$ alkyl, —C(O)—H, —S(O)$_2$—$C_1$-$C_6$ alkyl, —S(O)$_2$—H, —S(O)—$C_1$-$C_6$ alkyl, —S(O)—H and $C_1$-$C_6$ alkyl; and
$R_6$ is selected from the group consisting of hydrogen, —C(O)—$C_1$-$C_6$ alkyl, —C(O)—H, —S(O)$_2$—$C_1$-$C_6$ alkyl, —S(O)$_2$—H, —S(O)—$C_1$-$C_6$ alkyl, —S(O)—H and $C_1$-$C_6$ alkyl.

4. The compound of claim 1, wherein:
$R_3$ is selected from the group consisting of hydrogen, -Q-OR$_6$ and -Q-NR$_4$R$_5$;
Q is absent or (CH$_2$)$_n$, wherein n is 1, 2, 3, 4, 5 or 6;
$R_4$ and $R_5$ are independently selected from the group consisting of hydrogen, —C(O)—$C_1$-$C_6$ alkyl, —C(O)—H, —S(O)$_2$—$C_1$-$C_6$ alkyl, —S(O)$_2$—H, —S(O)—$C_1$-$C_6$ alkyl, —S(O)—H and $C_1$-$C_6$ alkyl; and
$R_6$ is selected from the group consisting of hydrogen and $C_1$-$C_6$ alkyl.

5. The compound of claim 1, wherein:
$R_1$ and $R_2$ are both deuterium;
$R_3$ is -Q-NR$_4$R$_5$; and
$R_4$ and $R_5$ are independently selected from the group consisting of hydrogen, —C(O)—$C_1$-$C_6$ alkyl, —C(O)—H, —S(O)$_2$—$C_1$-$C_6$ alkyl, —S(O)$_2$—H, —S(O)—$C_1$-$C_6$ alkyl, —S(O)—H and $C_1$-$C_6$ alkyl, wherein said $C_1$-$C_6$ alkyl is substituted with a substituent selected from the group consisting of halo, cyano, hydroxy, amino, mercapto, carboxy, sulfonic acid and sulfonic acid.

6. The compound of claim 1, wherein:
$R_1$ and $R_2$ are both deuterium;
$R_3$ is -Q-NR$_4$R$_5$;
Q is absent or (CH$_2$)$_n$, wherein n is 1, 2, 3, 4, 5 or 6; and
$R_4$ and $R_5$ are independently selected from the group consisting of hydrogen and $C_1$-$C_6$ alkyl.

7. The compound of claim 1, wherein:
$R_1$ and $R_2$ are both deuterium;
$R_3$ is -Q-NR$_4$R$_5$;
Q is absent; and
$R_4$ and $R_5$ are both hydrogen.

8. The compound of claim 1, wherein the compound is:

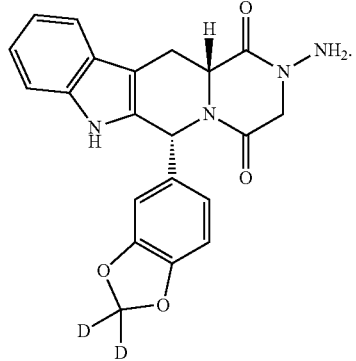

Compound DDCI-01

9. A pharmaceutical composition comprising a therapeutically effective amount of the compound of claim 1, or a pharmaceutically acceptable salt thereof, and a pharmaceutically acceptable carrier, excipient or diluent.

10. A method for modulating phosphodiesterase type 5 activity in a subject, comprising administering to the subject the compound of claim 1, or a pharmaceutically acceptable salt thereof.

11. The method of claim 10, wherein the subject is a human.

12. The method of claim 10, wherein the subject suffers from erectile dysfunction.

13. The method of claim 10, wherein the compound, or the pharmaceutically acceptable salt thereof, is administered to the subject via oral administration, buccal administration, sub-lingual administration, intravenous administration, intraperitoneal administration, subcutaneous administration, intramuscular administration, intradermal administration, inhalation administration or epidermal administration.

14. The method of claim 10, wherein the compound, or the pharmaceutically acceptable salt thereof, is formulated into tablets, dragees, lozenges, pills, capsules, granules, powders, solutions, emulsions, suspensions, dispersions, syrups, gels or aerosols.

\* \* \* \* \*